US010406136B2

(12) United States Patent
Park et al.

(10) Patent No.: US 10,406,136 B2
(45) Date of Patent: Sep. 10, 2019

(54) **COMPOSITION FOR SUPPRESSING NEURAMINIDASE ACTIVITY COMPRISING GERANYLATED FLAVONOID DERIVED FROM *PAULOWNIA TOMENTOSA* AS ACTIVE INGREDIENT**

(71) Applicants: INDUSTRY-ACADEMIC COOPERATION FOUNDATION GYEONGSANG NATIONAL UNIVERSITY, Jinju-si, Gyeongsangnam-do (KR); GWANGJU INSTITUTE OF SCIENCE AND TECHNOLOGY, Gwangju (KR)

(72) Inventors: Ki Hun Park, Jinju-si (KR); Soo Hyun Eom, Gwangju (KR); Young Bae Ryu, Gwangju (KR); Jung Keun Cho, Busan (KR)

(73) Assignees: INDUSTRY-ACADEMIC COOPERATION FOUNDATION GYEONGSANG NATIONAL UNIVERSITY, Jinji-si, Gyeongsangnam-Do (KR); GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 696 days.

(21) Appl. No.: 14/908,544

(22) PCT Filed: Jul. 25, 2014

(86) PCT No.: PCT/KR2014/006815
§ 371 (c)(1),
(2) Date: May 11, 2016

(87) PCT Pub. No.: WO2015/016539
PCT Pub. Date: Feb. 5, 2015

(65) Prior Publication Data

US 2016/0250179 A1 Sep. 1, 2016

(30) Foreign Application Priority Data

Jul. 29, 2013 (KR) ........................ 10-2013-0089727

(51) Int. Cl.
*A61K 36/00* (2006.01)
*A61K 31/353* (2006.01)
*A61K 36/80* (2006.01)
*A61K 36/185* (2006.01)
*A61K 45/06* (2006.01)

(52) U.S. Cl.
CPC .......... *A61K 31/353* (2013.01); *A61K 36/185* (2013.01); *A61K 36/80* (2013.01); *A61K 45/06* (2013.01); *A61K 2236/33* (2013.01)

(58) Field of Classification Search
CPC ...................................................... A61K 36/00
See application file for complete search history.

(56) References Cited

FOREIGN PATENT DOCUMENTS

| | | | | |
|---|---|---|---|---|
| CN | 102038079 | A | * | 5/2011 |
| KR | 20090129016 | A | | 12/2009 |
| KR | 20100114674 | A | | 10/2010 |
| KR | 20110057010 | A | | 5/2011 |

OTHER PUBLICATIONS

Cho et al, C-Geranyl flavonoids from Paulownia tomentosa fruits displaying potent neuraminidase inhibition. Abstracts of Papers, 239th ACS National Meeting, San Francisco, CA, United States, Mar. 21-25, 2010 (2010), AGFD-161. American Chemical Society: Washington, D. C. (Year: 2010).*

Dao, C-Methylated Flavonoids from Cleistocalyx operculatus and Their Inhibitory Effects on Novel Influenza A (H1N1) Neuraminidase. Journal of natural products, (Oct. 22, 2010) vol. 73, No. 10, pp. 1636-1642 (Year: 2010).*

Maywald et al, Evidence for the contribution of the host species to the extent of antigenic variation of N1 influenza virus neuraminidase. Medical microbiology and immunology, (1983) vol. 172, No. 1, pp. 1-11 (Year: 1983).*

Shinya et al. "Influenza virus receptors in the human airway", Nature, Mar. 2006, vol. 440, pp. 435-436, Nature Publishing Group.

Vimr E. et al. "To sialtlate, or not to sialylate: that is the question", Trends in Microbiology, Jun. 2002, vol. 10 No. 6, pp. 254-257.

Schauer, R. "Achievements and Challenges of Sialic Acid Research", Glycoconjugate Journal, Jan. 2000, Journal 17, 16 pages.

Taylor, G., "Sialidases: structures, biological significance and therapeutic potential", Current Opinion in Structural Biology, 1996, pp. 830-837.

Hein T.T. et al., "Avian Influenza A (H5N1) in 10 Patients in Vietnam", The New England Journal of Medicine, Mar. 18, 2004, vol. 350 No. 12, p. 1179-1188.

Soong, G. et al. "Baterial Neuraminidase Facilitates Mucosal Infection by Participating in Biofilm Production", The Journal of Clinical Investigation, vol. 116 No. 8, Aug. 2006, pp. 2297-2305.

Bantia, S et al. "Anti-influenza virus activity of peramivir in mice with single intramuscular injection", Antiviral Research, vol. 69, 2006, pp. 39-45.

Ryan, D. M et al., "GG167 (4-Guanidino-2, 4-Dideoxy-2, 3-Dehydro-N-Acetylneuraminic Acid) Is a Potent Inhibitor of Influenza Virus in Ferrets", Antimicrobial Agents and Chemotherapty, Nov. 1995, pp. 2583-2584.

(Continued)

*Primary Examiner* — Qiuwen Mi
(74) *Attorney, Agent, or Firm* — Hauptman Ham, LLP

(57) ABSTRACT

The present invention relates to a composition for suppressing neuraminidase activity comprising a geranylated flavonoid derived from *Paulownia tomentosa* as an active ingredient. The *Paulownia tomentosa* extract and the geranylated flavonoid isolated therefrom exhibit an effect in significantly suppressing neuraminidase, which is an enzyme that plays an important role in the occurrence of pathogenic viral and bacterial infections and of the inflammation that accompanies such infection, and thus the *Paulownia tomentosa* extract or the geranylated flavonoid isolated therefrom can advantageously be used as an active ingredient in a composition for inhibiting neuraminidase activity.

7 Claims, 13 Drawing Sheets

(56) References Cited

OTHER PUBLICATIONS

Cho, Jung Keun, "Competitive Neuraminidase Inhibitor Flavonoids from Paulownia tomentosa Fruits", Master's Thesis, Feb. 2010, 83 pages.

Cho, Jung Keun, "Geranylated flavonoids from Paulownia tomentosa inhibiting acetylcholinesterase and B-secretase enzyme associated with Alzheimer's Disease", Doctoral Thesis, Feb. 2013, 169 pages.

International Search Report dated Nov. 13, 2014 corresponding to International Application No. PCT/KR2014/006815.

* cited by examiner

| | | | | |
|---|---|---|---|---|
| **1** | $R^1 = OCH_3$, | $R^2 = OH$, | $R^3 = H$, | $R^4 = OH$ |
| **2** | $R^1 = OH$, | $R^2 = OCH_3$, | $R^3 = H$, | $R^4 = OH$ |
| **3** | $R^1 = OH$, | $R^2 = OCH_3$, | $R^3 = OH$, | $R^4 = OH$ |
| **4** | $R^1 = OCH_3$, | $R^2 = OH$, | $R^3 = H$, | $R^4 = H$ |
| **5** | $R^1 = OH$, | $R^2 = OCH_3$, | $R^3 = H$, | $R^4 = H$ |
| **6** | $R^1 = OH$, | $R^2 = OCH_3$, | $R^3 = OH$, | $R^4 = H$ |
| **7** | $R^1 = H$, | $R^2 = OH$, | $R^3 = H$, | $R^4 = H$ |
| **8** | $R^1 = OH$, | $R^2 = OH$, | $R^3 = H$, | $R^4 = H$ |
| **9** | $R^1 = OCH_3$, | $R^2 = OH$, | $R^3 = OCH_3$, | $R^4 = H$ |

COMPOSITION FOR SUPPRESSING NEURAMINIDASE ACTIVITY COMPRISING GERANYLATED FLAVONOID DERIVED FROM *PAULOWNIA TOMENTOSA* AS ACTIVE INGREDIENT

CROSS REFERENCE TO RELATED APPLICATION

This application claims the priority of Korean Patent Application No. 10-2013-0089727, filed on Jul. 29, 2013 in the KIPO (Korean Intellectual Property Office). Further, this application is the National Phase application of International Application No. PCT/KR2014/006815 filed Jul. 25, 2014, which designates the United States and was published in Korea.

TECHNICAL FIELD

The present invention relates to a composition for inhibiting neuraminidase activity comprising geranylated flavonoids derived from *Paulownia tomentosa.*

BACKGROUND ART

*Paulownia tomentosa* is native to Ullung Island of Korea and is a deciduous, broad-leaved tree belonging to family Paulowniacese, which grows naturally and broadly around Korea. It has large and broad oval shaped leaves with sharp tips and white downy hairs. The flowers are produced on panicles with a bell-shaped corolla and characterized by petals with purple stripes. This tree is distributed widely throughout Korea, China and Japan. Traditional Korean medicine has reported that the bark of *Paulownia tomentosa* can be used to treat gonorrhea, bruises, and the like, to enrich hair, and to accelerate hair production. It has been also reported that the bark of *Paulownia tomentosa* can be used as a deodorizer.

Up to now, ingredients known from *Paulownia tomentosa* include catapol, syringin, aucubin, coniferin, acteoside, paulownin which is a lignan, sesamin, (+)-piperitol, ursolic acid which is a triterpenoid, and the like.

Neuraminidase among saccharide hydrolase enzymes hydrolyzes sialic acids occurring at saccharide complexes on the surfaces of cells, particularly at the terminal of glycoproteins. Neuraminidase (NA) hydrolyzes acetal linkages between galactose and sialic acids which are constitutional components of glycoproteins, particularly selectively hydrolyzes α 2,3- and α 2,6-positions (Shinya et al. *Nature* 2006, 440, 435). Neuraminidase is found in higher eukaryotes and various sorts of pathogenic viruses and bacteria (Vimr, E.; Lichtensteiger, C. *Trends Microbiol.* 2002, 10, 254; Schauer, R. *Glycoconjugate J.* 2000, 17, 485; Taylor, G. L. *Curr. Opin. Struct. Biol.* 1996, 6, 830). The hydrolysis of sialic acids by neuraminidase plays a key role in cell-cell signaling and cell-cell factors.

Influenza is a very infectious virus causing acute respiratory diseases and causes global mass infection or severe respiratory symptoms in infants, the elderly, and cardiorespiratory disease patients (Hien, T. T. et al. *N. Eng. J. Med.,* 350, 1179, 2004). Influenza taxonomically belongs to family Orthomyxovirus and can be divided into three types, namely type A, type B and type C. In particular epidemically spread viruses are types A and B. In the case of influenza, a viron that is proliferated in infected host cells attaches to sialic acids at the terminal of glycoproteins on the cell membrane. Hydrolysis of sialic acids and viron by means of neuraminidase may spread viruses to new cells, wherein the inhibition of neuraminidase function can prevent the spread of viruses. Accordingly, neuraminidase inhibitors are utilized as components for antivirals.

On the other hand, production of biofilms is a core procedure when pathogenic bacteria infect host cells. Neuraminidase serves as a key enzyme for biofilm production. In this context, inhibition of neuraminidase function may inhibit biofilm production, which in turn prevents bacterial infections (Soong, G. et al., *J. Clin. Invest.* 2006, 116, 2297). *Streptococcus pneumonia, Pseudomonas aeruginosa, Clostridium perfringen* and the like are representative pathogenic bacteria that infect host cells through biofilm production by neuraminidase. Further, sialic acids are closely related to immune responses. Generally, after viral or bacterial infection, sialic acids occurring on saccharide complexes on the surfaces of cells are hydrolyzed by neuraminidase, which activates intracellular cytokines and the like and precedes inflammation, thereby causing sepsis. Therefore, neuraminidase inhibitors are effective in preventing and treating infections by pathogenic viruses and bacteria and inflammatory diseases caused by such infections.

Multilateral research has been globally performed in order to develop influenza virus therapeutic agents. Representative influenza virus therapeutic agents include four substances, namely, amatadine, rimatadine, zanamivir, and oseltamivir, which are approved by the US Food and Drug Administration (FDA). The drugs amatadine and rimatadine are M2 inhibitors that have antiviral activity by inhibiting uncoating of viruses through blocking ion channels of M2 proteins as cell membrane proteins which are essential to viral propagation, and only helpful in relieving symptoms of influenza type A. Having been used for 40 years, viruses having resistance to these drugs have appeared and been reported to show severe side effects in the nervous system and stomach (Bantia, S. et al. *Antiviral Research* 69, 39, 2006). Since 1999, treatments of viral infection using new drugs such as zanamivir and oseltamivir have been reported, wherein those drugs are neuraminidase inhibitors stably existing in both influenza types A and B, play an important role in viral propagation, and are less likely to generate resistance (Zhang, J. et al. Bioorg. Med. Chem. Lett. 16, 3009, 2006). However, although zanamivir has high antiviral effects, it has demerits of low bioavailability and fast exclusion from the kidneys (Ryan, D. M. et al. Antimicrob. Agents Chemother., 39, 2583, 1995). Further, oseltamivir has been reported to have side effects of severe nausea.

Antiviral agents developed up to now have severe side effects and thus require meticulous care in application thereof. Since development of vaccines has problems of low effect if virus type of epidemic influenza does not match virus type of vaccines, there is a need for a new anti-influenza viral drug based on natural substances having a good infection inhibitory effects and good stability.

The inventors of the present invention have isolated geranylated flavonoids from an extract of *Paulownia tomentosa* and identified structures thereof. In addition, the present inventors have examined whether the isolated geranylated flavonoids have activity against neuraminidase which plays an important role in inflammation induced by pathogenic virus and bacterium infections and found that the isolated geranylated flavonoids exhibit significant neuraminidase inhibition activity and the extract of *Paulownia tomentosa* and geranylated flavonoids isolated from the extract can be effectively utilized in a composition for inhibiting neuraminidase activity. Based on this finding, the present invention has been achieved.

DISCLOSURE

Technical Problem

It is an aspect of the present invention to provide a composition for inhibiting neuraminidase activity containing an extract of *Paulownia tomentosa* or geranylated flavonoids derived from *Paulownia tomentosa* as an active ingredient.

Technical Solution

The present invention provides a pharmaceutical composition for inhibiting neuraminidase activity containing an extract of *Paulownia tomentosa* as an active ingredient.

In addition, the present invention provides a pharmaceutical composition for inhibiting neuraminidase activity, containing a compound represented by Formula 1 or a pharmaceutically acceptable salt thereof as an active ingredient.

[Formula 1]

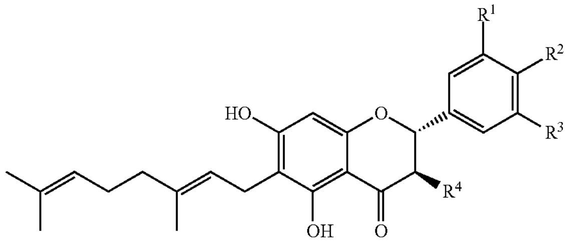

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Further, the present invention provides a health food composition for inhibiting neuraminidase activity containing an extract of *Paulownia tomentosa* or a fraction thereof as an active ingredient.

Further, the present invention provides a health food composition for inhibiting neuraminidase activity containing a compound represented by Formula 1 or a pharmaceutically acceptable salt thereof as an active ingredient.

Further, the present invention provides a method for inhibiting neuraminidase activity, comprising: administering a pharmaceutically effective amount of an extract of *Paulownia tomentosa* or a fraction thereof to an individual.

Further, the present invention provides a method for inhibiting neuraminidase activity, comprising: administering a pharmaceutically effective amount of a compound represented by Formula 1 or a pharmaceutically acceptable salt thereof to an individual.

[Formula 1]

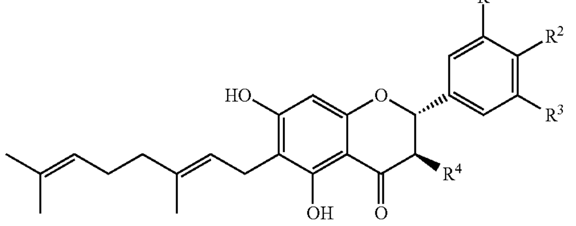

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Further, the present invention provides a use of an extract of *Paulownia tomentosa* or a fraction thereof for a pharmaceutical composition for inhibiting neuraminidase activity.

Further, the present invention provides a use of an extract of *Paulownia tomentosa* or a fraction thereof for a health food composition for improving neuraminidase activity inhibition.

Further, the present invention provides a use of a compound represented by Formula 1 or a pharmaceutically acceptable salt thereof for a pharmaceutical composition for inhibiting neuraminidase activity.

[Formula 1]

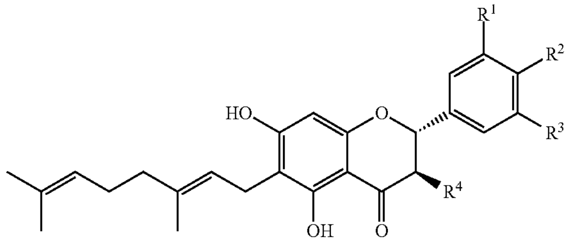

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Further, the present invention provides a use of a compound represented by Formula 1 or a pharmaceutically acceptable salt thereof for a health food composition for improving neuraminidase activity inhibition.

[Formula 1]

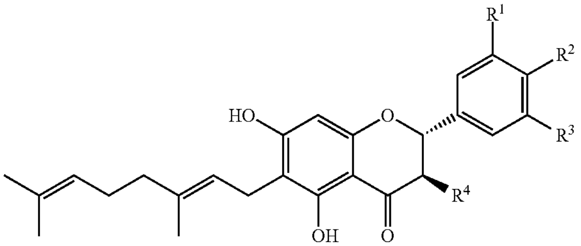

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Further, the present invention provides a pharmaceutical composition for treating viral or bacterial inflammatory diseases, comprising: an extract of *Paulownia tomentosa* or a fraction thereof as an active ingredient.

Further, the present invention provides a health food composition for improving viral or bacterial inflammatory diseases, containing an extract of *Paulownia tomentosa* or a fraction thereof as an active ingredient.

Further, the present invention provides a pharmaceutical composition for treating viral or bacterial inflammatory diseases, containing: a compound represented by Formula 1 or a pharmaceutically acceptable salt thereof as an active ingredient.

[Formula 1]

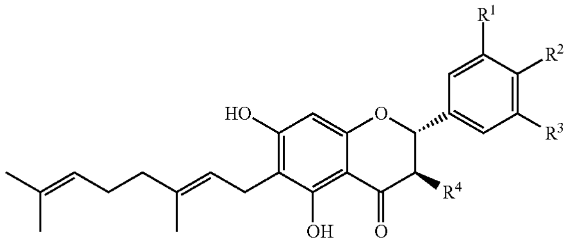

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Further, the present invention provides a health food composition for improving viral or bacterial inflammatory diseases, containing: a compound represented by Formula 1 or a pharmaceutically acceptable salt thereof as an active ingredient.

[Formula 1]

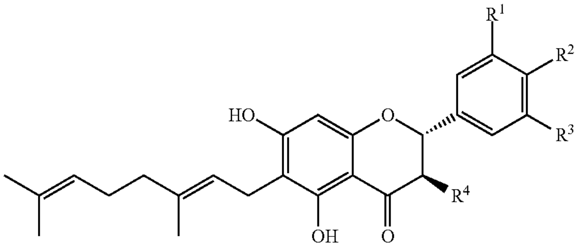

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Further, the present invention provides a method for treating viral or bacterial inflammatory diseases using an extract of *Paulownia tomentosa* or a fraction thereof as an active ingredient.

Further, the present invention provides a method for treating viral or bacterial inflammatory diseases using a compound represented by Formula 1 or a pharmaceutically acceptable salt thereof as an active ingredient.

[Formula 1]

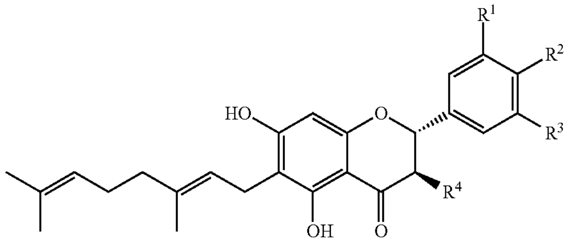

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Further, the present invention provides a use of an extract of *Paulownia tomentosa* or a fraction thereof for a pharmaceutical composition for treating viral or bacterial inflammatory diseases.

Further, the present invention provides a use of an extract of *Paulownia tomentosa* or a fraction thereof for a health food for improving viral or bacterial inflammatory diseases.

Further, the present invention provides a use of a compound represented by Formula 1 or a pharmaceutically acceptable salt thereof for a pharmaceutical composition for treating viral or bacterial inflammatory diseases.

[Formula 1]

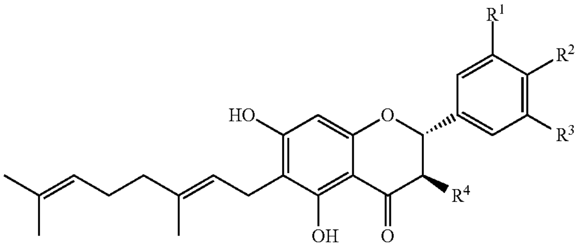

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

In addition, the present invention provides a use of a compound represented by Formula 1 or a pharmaceutically acceptable salt thereof for a health food for improving viral or bacterial inflammatory diseases.

[Formula 1]

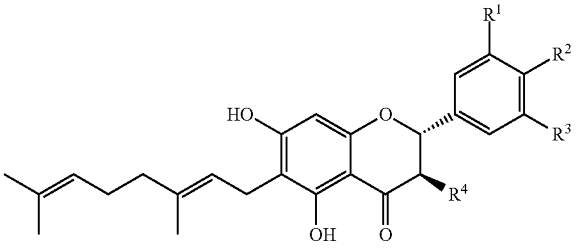

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

Advantageous Effects

The present invention relates to a pharmaceutical composition for inhibiting neuraminidase activity containing an extract of *Paulownia tomentosa* or geranylated flavonoids derived from the extract as an active ingredient. The extract of *Paulownia tomentosa* or geranylated flavonoids derived from the extract exhibit significant inhibition activity for neuraminidase, which plays an important role in inflammation associated with pathogenic viral and bacterial infections. Therefore, the extract of *Paulownia tomentosa* or geranylated flavonoids derived from the extract can be effectively used in a composition for inhibiting neuraminidase activity for preventing and treating influenza infection.

BEST MODE

Figure 1:
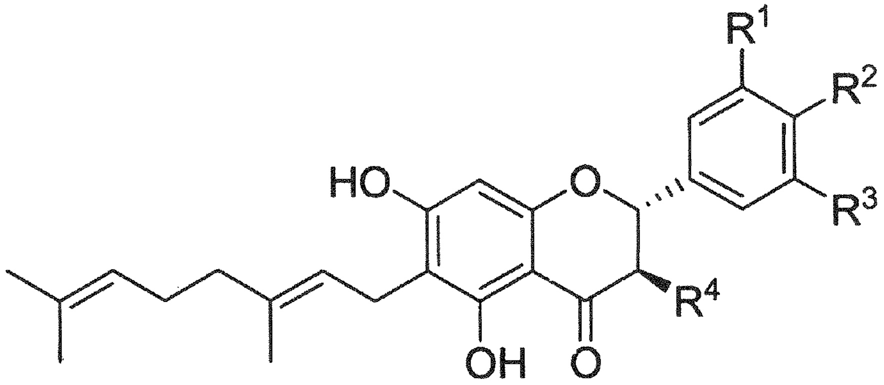
FIG. 1 shows chemical structures of effective components of an extract of *Paulownia tomentosa.*

Hereinafter, the present invention will be described in more detail.

The present invention provides a pharmaceutical composition for inhibiting neuraminidase activity containing an extract of *Paulownia tomentosa* as an active ingredient.

The extract of *Paulownia tomentosa* may be prepared by a method comprising the following steps, without being limited thereto.

1) performing extraction by adding a solvent for extracting *Paulownia tomentosa* to obtain an extract;

2) filtering the extract obtained in step 1);

3) concentrating and drying the filtered extract of step 2) under reduced pressure to prepare an extract of *Paulownia tomentosa;*

4) further performing extraction by adding an organic solvent to the extract of *Paulownia tomentosa* of step 3) to yield a fraction of *Paulownia tomentosa.*

In the above method, *Paulownia tomentosa* in step 1) may be cultivated or commercially purchased, without any limitation. The leaves, barks, roots or fruits of *Paulownia tomentosa* may be used, without being limited thereto. Most preferably, fruits of *Paulownia tomentosa* are used.

In the above method, the extraction solvent in step 1) may be water, alcohols or mixtures thereof. As an alcohol, it is preferable to use a $C_1$ to $C_2$ lower alcohol. As a lower alcohol, ethanol or methanol may be used. As an extraction method, shaking extraction, Soxhlet extraction or reflux extraction may be used, without being limited thereto. Extraction is performed by adding 1 to 10 times, preferably 4 to 6 times of an extraction solvent to a dried *Paulownia tomentosa* portion. Extraction may be carried out at 20° C. to 100° C., more preferably at 20° C. to 40° C., most preferably at room temperature, without being limited thereto. The extraction time may be 10 hours to 48 hours, more preferably 15 hours to 30 hours, most preferably 24 hours, without being limited thereto. Extraction may be repeated one to 5 times, more preferably 3 times to 4 times, most preferably 3 times, without being limited thereto.

In this method, concentration under reduced pressure in step 3) may be performed using a vacuum reduced pressure evaporator or a vacuum rotary evaporator, without being limited thereto. In addition, drying is performed by reduced pressure drying, vacuum drying, boiling drying, spray drying or freeze drying, without being limited thereto.

In this method, as the extract of *Paulownia tomentosa* in step 4), a dark brown crude extract obtained by concentrating the extract of *Paulownia tomentosa* under reduced pressure may be used, without being limited thereto. In addition, n-hexane, chloroform, ethyl acetate or butanol may be used as an organic solvent. According to one exemplary embodiment, the organic solvent is chloroform, without being limited thereto. The fraction may be n-hexane fractions, chloroform fractions, ethyl acetate fractions, butanol fractions or water fractions obtained by suspending the extract of *Paulownia tomentosa* in water, followed by sequentially fractionating using n-hexane, chloroform, ethyl acetate, butanol and water, without being limited thereto. The fractions are obtained by repeatedly fractionating the extract of *Paulownia tomentosa* 1 to 5 times, preferably 3 times. The fractions may be concentrated under reduced pressure after fractionation, without being limited thereto.

Neuraminidase may be derived from viruses, bacteria or humans, without being limited thereto.

Viruses may be influenza A virus subtype H1N1, influenza B virus subtype H1N1, or influenza C virus subtype H1N1, without being limited thereto.

Bacteria may be *Clostridium perfringens*, without being limited thereto.

In addition, the present invention provides a pharmaceutical composition for inhibiting neuraminidase activity containing, as an active ingredient, a fraction obtained by further fractionating the extract of *Paulownia tomentosa* with an organic solvent.

The organic solvent may be n-hexane, ethyl acetate or n-butanol, each of which exhibits neuraminidase inhibition activity, without being limited thereto.

In some examples, the inventors obtained a dark brown crude extract by concentrating the extract of *Paulownia tomentosa* with methanol under reduced pressure. The dark brown crude extract was subjected to fractionation using ethyl acetate. In addition, geranylated flavonoid derivatives were isolated from the obtained fractions and structures thereof were analyzed (FIGS. 5 to 13).

Furthermore, in order to identify neuraminidase inhibition activity of effective components (compounds 1 to 9) of the extract of *Paulownia tomentosa*, the extract of *Paulownia tomentosa* was added to cells and then subjected to fluorescence analysis using SpectraMax M3. As a result, it was confirmed that geranylated flavonoid (compounds 1 to 9) isolated from fruits of *Paulownia tomentosa* inhibited neuraminidase activity depending upon concentration (see Table 1 and FIG. 2).

In order to identify neuraminidase inhibition activity of effective components (compounds 1 to 9) of the extract of *Paulownia tomentosa*, reactions between various concentrations of a substrate and an inhibitor were analyzed as fluorescence values using results of <Experimental Example 1>. Lineweaver-Burk and Dixon plots revealed that changes in experiments at different enzyme concentrations and inhibitor concentrations were represented by straight lines, and these straight lines met at an identical intersection point on the y-axis, which showed that all compounds were reversible enzyme inhibitors (see FIG. 3).

In order to identify neuraminidase inhibition activity of effective components (compounds 1 to 9) of the extract of *Paulownia tomentosa*, reactions between various concentration of a substrate and an inhibitor were analyzed as fluorescence values using results of <Experimental Example 1>. Lineweaver-Burk and Dixon plots revealed that the straight lines of reaction speed (140 according to the concentration of inhibitor (1/[S]) met at an identical intersection point on 1/v (y-axis). It could be seen that Compounds 1 to 9 were typical competitive inhibitors in which Vmax did not change while Km declined (see FIG. 4).

As such, the extract of *Paulownia tomentosa* or fraction thereof exhibits significant neuraminidase inhibition activity, and thus can be effectively used in a composition for preventing or treating influenza infection and inhibiting neuraminidase activity.

The composition containing the extract of *Paulownia tomentosa* according to the present invention may further include at least one active ingredient exhibiting identical or similar functions.

The composition according to the present invention may further include a pharmaceutically acceptable additive. As the pharmaceutically acceptable additive, starches, gelatinized starches, non-crystalline cellulose, lactose, povidone, colloidal silicone dioxide, calcium hydrogen phosphate, lactose, mannitol, taffy, gum arabic, pregelatinized starch, corn starch, powdered cellulose, hydroxypropylcellulose, Opadry, sodium starch glycol, carnauba lead, synthetic aluminum silicate, stearic acid, magnesium stearate, aluminum stearate, calcium stearate, sucrose, dextrose, sorbitol, talc and the like may be used. The pharmaceutically acceptable additive according to the present invention may be present in an amount of 0.1 parts by weight to 90 parts by weight, without being limited thereto.

Namely, the composition according to the present invention may be administered in various dosage forms in oral administration and parenteral administration upon actual clinical administration. In formulation, diluents or excipients such as commonly used fillers, thickening agents, binders, wetting agents, disintegrating agents, surfactants, and the like may be used to prepare formulations. As a solid formulation for oral administration, tablets, pills, powders, granules, capsules, and the like may be included. Such solid formulation may be prepared by mixing an extract of *Carpesium cernuum* L. with at least one excipient, for example, starch, calcium carbonate, sucrose, lactose, gelatin or the like. In addition to simple excipients, lubricants such as magnesium stearate, talc, and the like may be used. As a liquid preparation for oral administration, suspensions, solutions, emulsions, syrups, and the like may be used. The composition may further include various excipients, for example, wetting agents, sweeteners, flavoring agents, and preserving agents, as well as simple diluents such as water, liquid paraffin, and the like. Preparations for parenteral administration may include sterilized aqueous solutions, non-aqueous solvents, suspensions, emulsions, lyophilizing agents, and suppositories. As a non-aqueous solvent and suspending solvent, vegetable oils such as propylene glycol, polyethylene glycol, olive oil, injectable esters such as ethyl oleate and the like may be used. As a base for suppositories, Witepsol, Microgol, Tween 61, cacao butter, laurinum, glycerogelatin, and the like may be used.

The composition according to the present invention may be administered orally or parenterally depending upon intended usage. For parenteral administration, it is preferable to select topical use or intraperitoneal injection, rectal injection, subcutaneous injection, venous injection, intramuscular injection or breast injection. Dose amount may be varied depending upon body weight, age, gender, health condition, diet of patients, administration time, administration method, excretion rate, disease severity and the like.

The composition according to the present invention may be administered in a pharmaceutically effective amount. In the present invention, the "pharmaceutically effective amount" refers to an amount sufficient to treat diseases within reasonable risk-benefit ratio applicable for medical treatment. Effective dosage level may be determined in accordance with an element comprising disease types and severity of patients, activity of drugs, sensitivity to drugs, administration time, administration routes and excretion rate, treatment time, simultaneously administered drugs and other elements well known in medical applications. The composition according to the present invention may be administered as an individual treatment agent or in combination with other therapeutic agents. The composition according to the present invention may be administered sequentially or simultaneously with prior therapeutic agents in single or multiple administrations. The composition needs to be administered in a minimal amount to obtain maximum effects without side effects, considering the aforementioned elements, which can be easily determined by those skilled in the art.

Specifically, the effective amount of the compounds according to the present invention may be varied depending upon age, gender, and body weight of patients. Generally, the compounds of the present invention are administered in an amount of 0.1 mg to 100 mg/kg body weight, preferably 0.5 mg to 10 mg/kg body weight daily or every other day once to three times per day. The effective amount may be increased or reduced according to dose routes, severity of obesity, age, body weight, age, and the like. However, the dosage amount does not restrict the scope of the present invention in any way.

The present invention provides a pharmaceutical composition for inhibiting neuraminidase activity containing a compound represented by Formula 1 or a pharmaceutically acceptable salt thereof as an active ingredient.

[Formula 1]

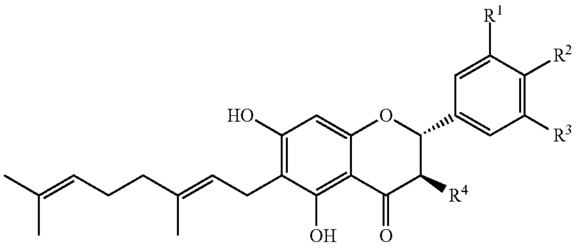

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be used in the form of pharmaceutically acceptable salt thereof. As a salt, an acid addition salt formed using a pharmaceutically acceptable free acid is preferred, without being limited thereto.

The compound represented by Formula 1, which is isolated from the extract of *Paulownia tomentosa*, may exhibit neuraminidase inhibition activity, without being limited thereto.

The compound represented by Formula 1 exhibits neuraminidase inhibition activity and is one selected from the group consisting of compounds of Formulae 2 to 10, without being limited thereto.

[Formula 2]

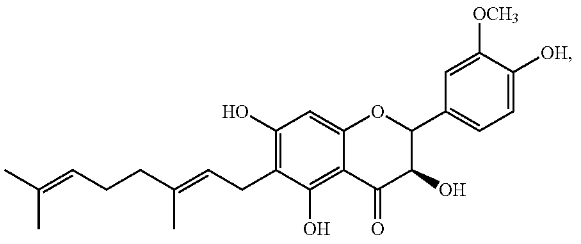

[Formula 3]

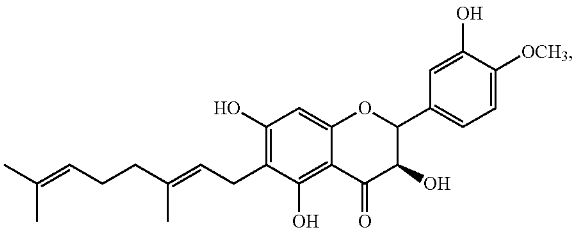

[Formula 4]

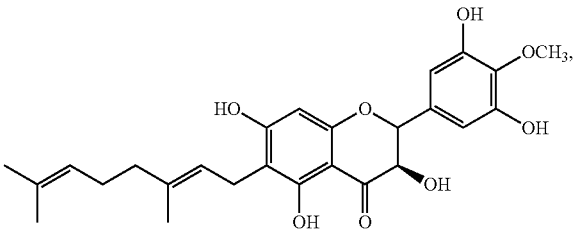

-continued

[Formula 5]

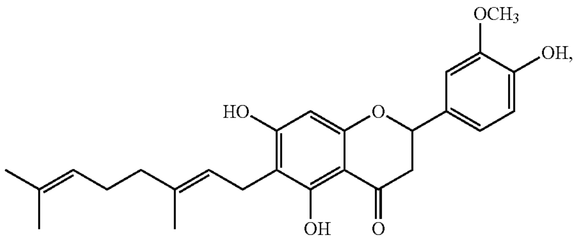

[Formula 6]

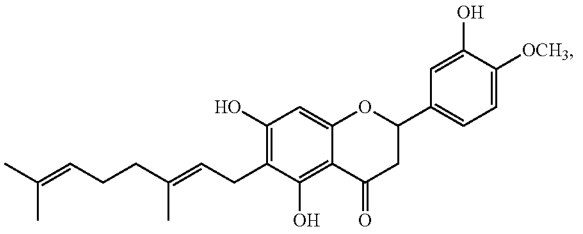

[Formula 7]

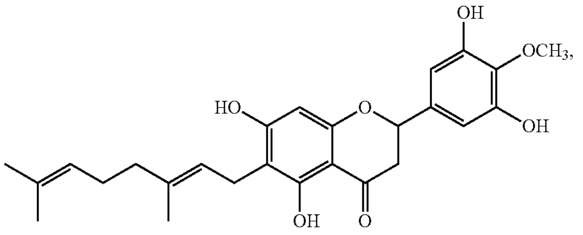

[Formula 8]

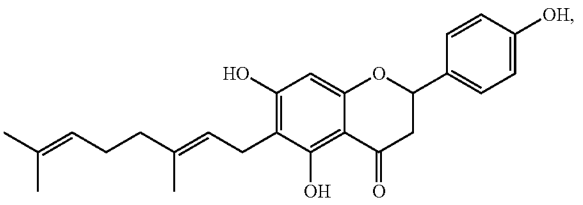

[Formula 9]

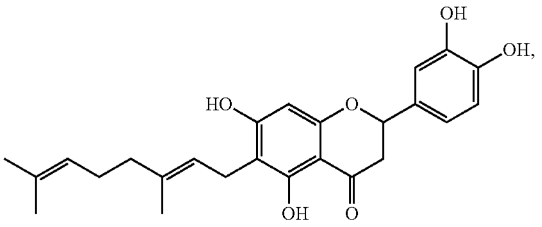

and

[Formula 10]

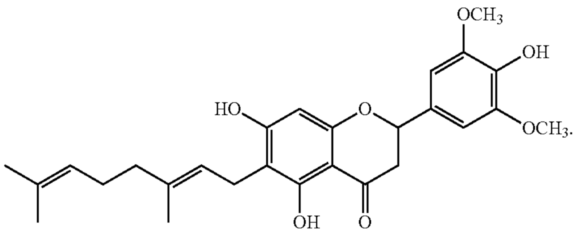

These compounds may have an inhibition activity of a neuraminidase derived from influenza A virus subtype H1N1, influenza B virus subtype H1N1, *Clostridium perfringens* or humans, without being limited thereto.

The geranylated compounds derived from *Paulownia tomentosa* represented by Formulae 1 to 10 exhibits a significant neuraminidase inhibition effect and thus can be effectively used in a composition for preventing or treating influenza infections and inhibiting neuraminidase activity.

The present invention provides a health food for inhibiting neuraminidase activity containing an extract of *Paulownia tomentosa* or a fraction thereof as an active ingredient.

The fraction may be prepared by fractionating the fraction of *Paulownia tomentosa* with an organic solvent, without being limited thereto.

Since the extract of *Paulownia tomentosa* or the fraction thereof exhibits significant neuraminidase inhibition activity, the extract of *Paulownia tomentosa* can be effectively used in a health food composition for inhibiting neuraminidase activity.

The sort of foods is not particularly limited. Examples of foods to which the above compounds can be added may include various foods such as snacks, breads, noodles, and the like, drinks such as water, soft drinks, fruit drinks and the like, gums, teas, vitamin complexes, seasonings, functional health foods, and the like.

The extract of *Paulownia tomentosa* of the present invention may be added to foods as is or together with other foods or food components. The extract of *Paulownia tomentosa* of the present invention may be suitably used according to typical methods. The mixing amount of active ingredients may be suitably determined depending upon purpose of use (prevention or improving). In general, the amount of the compounds in health foods is 0.01 wt % to 15 wt %, preferably 0.1 wt % to 5 wt %, based on the total food weights. The compounds of the present invention are added in an amount of 0.01 g to 5.0 g, preferably 0.01 g to 1.0 g, based on 100 g of health drink composition. However, for long-term use for health adjustment, the amount may be less than the lower limit. The effective components may be used in an amount greater than the above range since the effective components have no problem in view of stability.

The health functional drink composition according to the present invention is not limited in view of other components except that the composition contains the compounds according to the present invention as essential components in a predetermined ratio. Like typical drinks, the composition may further contain various flavoring agents or natural hydrocarbons as an additional component. Examples of natural hydrocarbons may include typical saccharides such as monosaccharides, for example, glucose and fructose; disaccharides, for example, maltose and sucrose; polysaccharides, for example, dextrin and cyclodextrin; and sugar alcohols such as xylitol, sorbitol and erythritol. In addition, as a flavoring agent, natural flavoring agents (taumakin, *stevia* extract, and the like), and synthetic flavoring agents (saccharin, aspartame, and the like) may be effectively used. The natural hydrocarbon is used in an amount of about 0.1 g to 2.0 g, preferably about 0.1 g to 1.0 g, based on 100 g of the composition according to the present invention.

The functional health foods of the present invention can be easily obtained by further comprising a process of adding an extract or a compound of the present invention as a base during a method for preparing foods or after the preparation of foods. If necessary, it is possible to add taste and odor masking agents.

The extract of *Paulownia tomentosa* or fractions thereof may include various nutritional agents, vitamins, minerals (electrolytes), flavoring agents such as synthetic flavoring agents and natural flavoring agents, coloring agents and enhancers (cheese, chocolate and the like), pectic acid and salts thereof, alginic acid and salts thereof, organic acids, protective colloid thickening agents, pH adjusting agents, stabilizers, antiseptic agents, glycerin, alcohols, carbonated drinks, and the like. In addition, the extract of *Paulownia tomentosa* or fractions thereof may contain natural fruit juice and fruit flesh for preparing fruit juice drinks and vegetable drinks. These components may be used alone or in combination. Although the amount of such additives is not critical, the additives are generally present in an amount of about 20 parts by weight, based on 100 parts by weight of the extract of *Paulownia tomentosa* or fractions thereof.

The present invention provides a health food composition for inhibiting neuraminidase activity containing a compound represented by Formula 1 or a pharmaceutically acceptable salt thereof as an active ingredient.

The compound represented by Formula 1 or the pharmaceutically acceptable salt thereof of the present invention exhibits neuraminidase inhibition activity, and thus the Formula 1-10 can be effectively used in a health food composition for inhibiting neuraminidase activity.

The derivatives represented by Formula 1 may be used in the form of pharmaceutically acceptable salts. As a salt, it is useful to employ an acid addition salt formed from a pharmaceutically acceptable free acid. The acid addition salt can be formed using inorganic acids such as hydrochloric acid, phosphoric acid, sulfuric acid, hydrobromic acid, hydroiodic acid, nitric acid or phosphoric acid and the like, non-toxic organic acids such as aliphatic mono- and dicarboxylates, phenyl-substituted alkanoates, hydroxyalkanoates and alkanedioates, aromatic acids, aliphatic and aromatic sulfonic acids and the like, organic acids such as acetic acid, benzoic acid, citric acid, lactic acid, maleic acid, gluconic acid, methanesulfonic acid, 4-toluenesulfonic acid, tartaric acid, fumaric acid, and the like. Examples of pharmaceutically non-toxic salts may include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprillates, acrylates, formats, isobutyrates, caprates, heptanoates, propiolates, oxalates, malonates, succinates, suberates, sebacates, fumarates, maleates, butane-1,4-dioates, hexane-1,6-dioates, benzoates, chlorobenzoates, methyl benzoates, dinitrobenzoates, hydroxybenzoates, methoxybenzoates, phthalates, terephthalates, benzene sulfonates, toluene sulfonates, chlorobenzene sulfonates, xylene sulfonate, phenylacetates, phenylpropionates, phenylbutyrates, citrates, lactates, β-hydroxybutyrates, glycolates, malates, tartarates, methanesulfonates, propanesulfonates, naphthalene-1-sulfonate, naphthalene-2-sulfonate, and mandelates.

The acid addition salts according to the present invention may be prepared by a typical method, for example, dissolving a derivative represented by Formula 1 in an organic solvent, for example, methanol, ethanol, acetone, methylene chloride, acetonitrile and the like, followed by adding an organic acid or an inorganic acid to form precipitates, and then filtering and drying the resultant precipitates, or subjecting a solvent and an excess of acid to distillation under reduced pressure and then drying or crystallizing the resultant mass in the presence of an organic solvent.

It is also possible to prepare a pharmaceutically acceptable metal salt by using a base. Alkali metal salts or alkaline earth metal salts may be obtained, for example, by dissolving a compound in an excess of alkali metal hydroxide or alkaline earth metal hydroxide solution, followed by filtering non-soluble compound salts, and then evaporating or drying the filtered liquid. As a metal salt, it is pharmaceutically preferred to prepare sodium, potassium or calcium salts. The corresponding silver salts can be obtained by reacting an alkali metal or alkaline earth metal salt with a suitable silver salt (for example, silver nitrate).

The present invention provides a method for inhibiting neuraminidase activity, comprising: administering a pharmaceutically effective amount of an extract of *Paulownia tomentosa* or a fraction thereof to an individual.

The present invention provides a method for inhibiting neuraminidase activity, comprising: administering a pharmaceutically effective amount of a compound represented by Formula 1 or a pharmaceutically acceptable salt thereof to an individual.

[Formula 1]

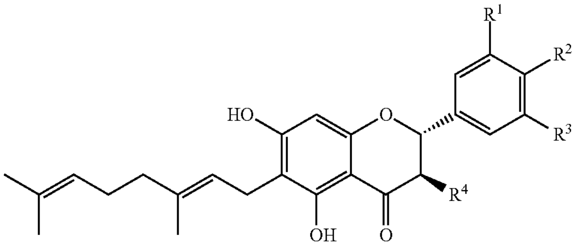

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

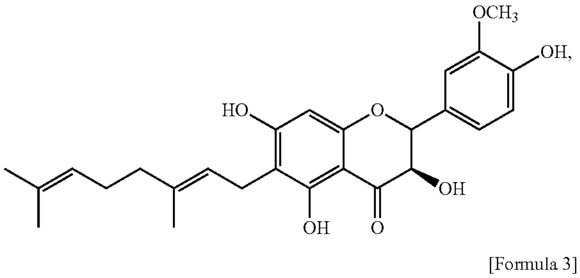

[Formula 3]

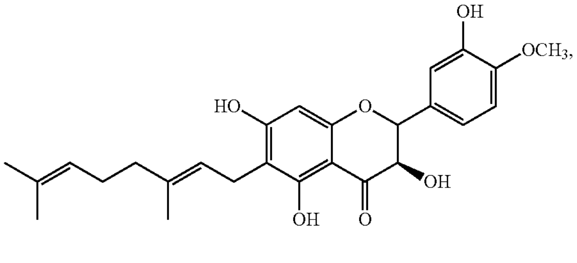

-continued

[Formula 4]

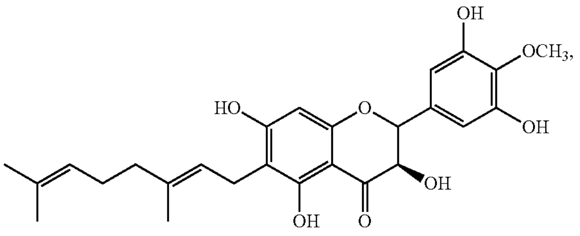

[Formula 5]

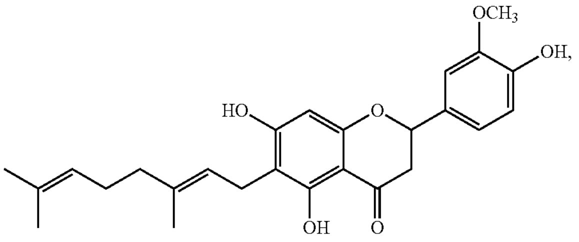

[Formula 6]

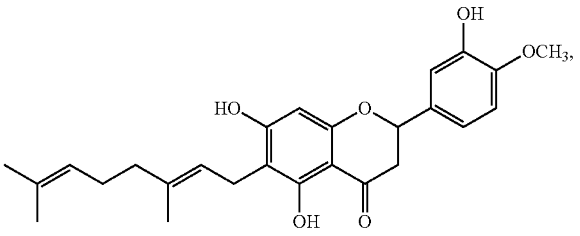

[Formula 7]

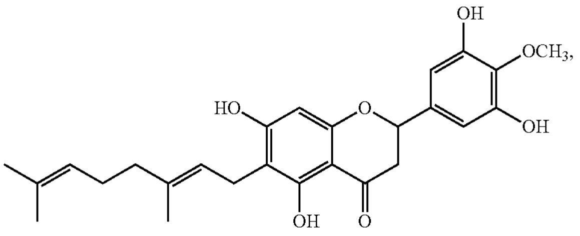

[Formula 8]

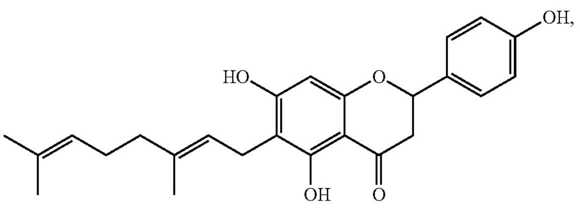

[Formula 9]

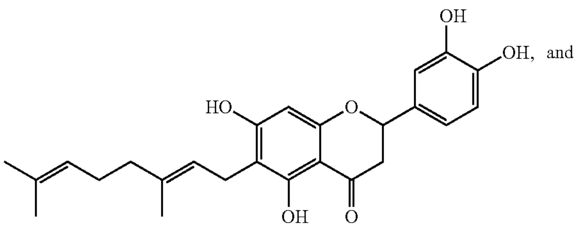

and

-continued

[Formula 10]

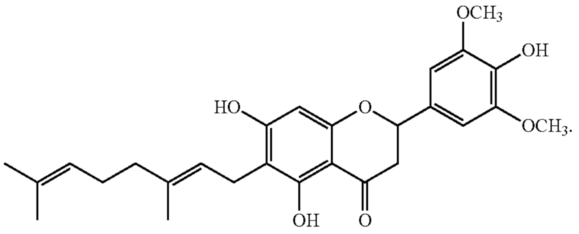

Further, the present invention provides a use of an extract of *Paulownia tomentosa* or a fraction thereof for a pharmaceutical composition for inhibiting neuraminidase activity.

Further, the present invention provides a use of an extract of *Paulownia tomentosa* or a fraction thereof for a health food for improving neuraminidase inhibition activity.

Further, the present invention provides a use of a compound represented by Formula 1 or a pharmaceutically acceptable salt thereof for a pharmaceutical composition for inhibiting neuraminidase activity.

[Formula 1]

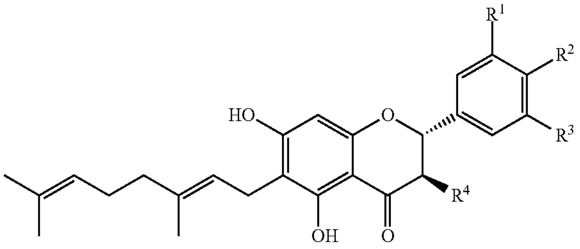

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

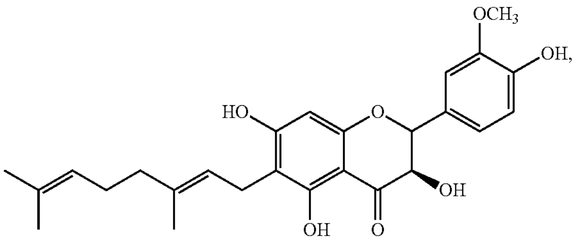

[Formula 3]

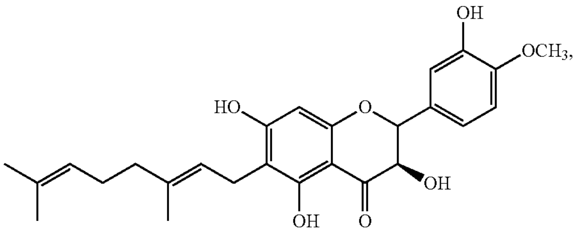

-continued

[Formula 4]

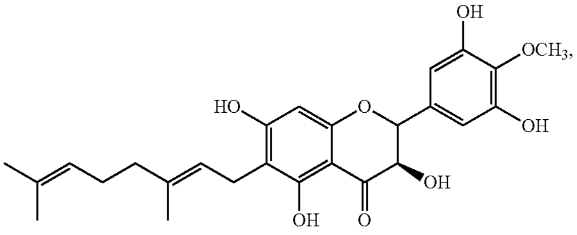

[Formula 5]

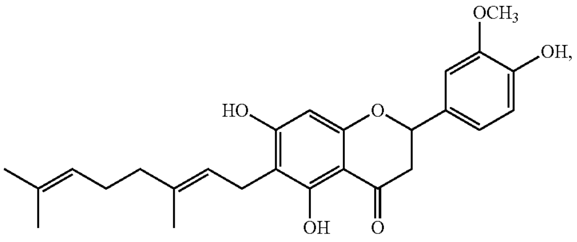

[Formula 6]

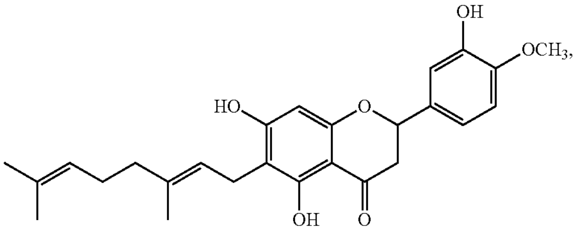

[Formula 7]

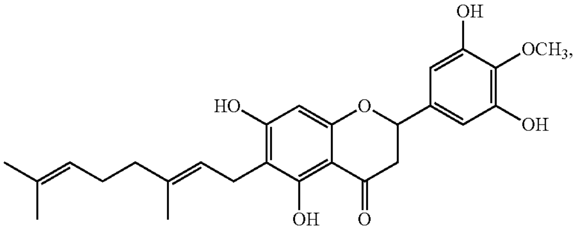

[Formula 8]

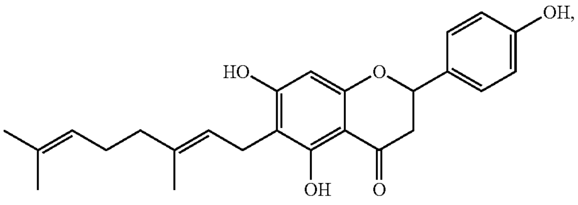

[Formula 9]

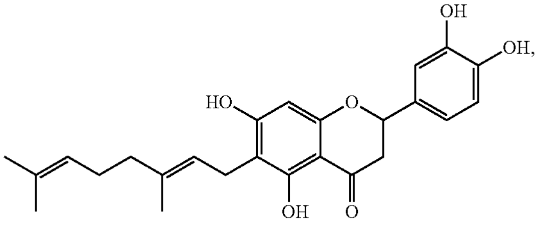

and

-continued

[Formula 10]

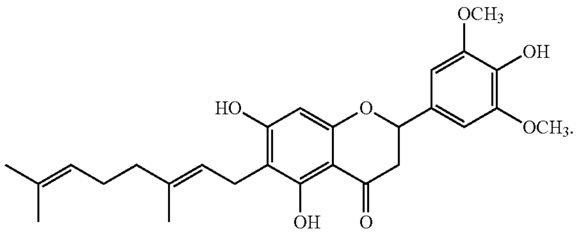

The present invention provides a use of a compound represented by Formula 1 or a pharmaceutically acceptable salt thereof for a health food for improving neuraminidase inhibition activity.

[Formula 1]

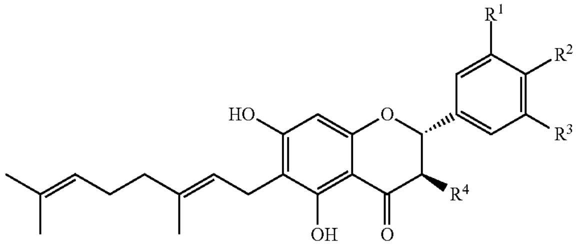

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

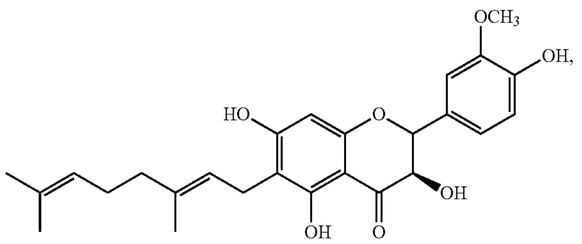

[Formula 3]

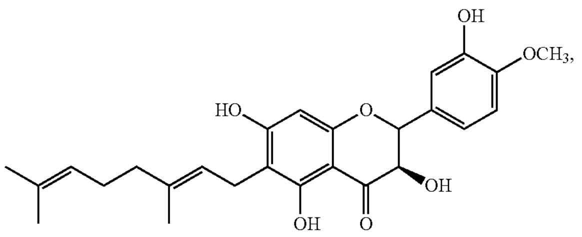

-continued

[Formula 4]

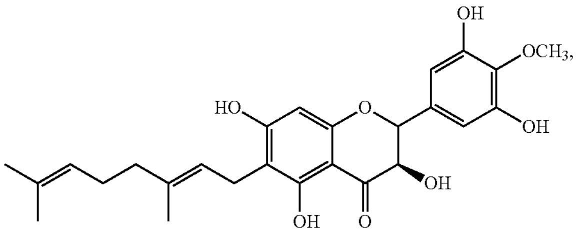

[Formula 5]

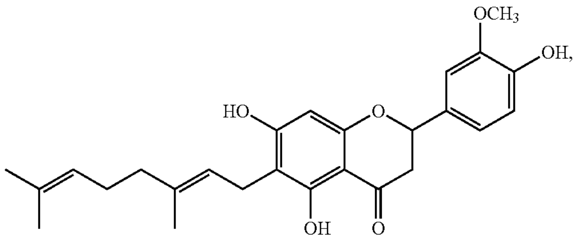

[Formula 6]

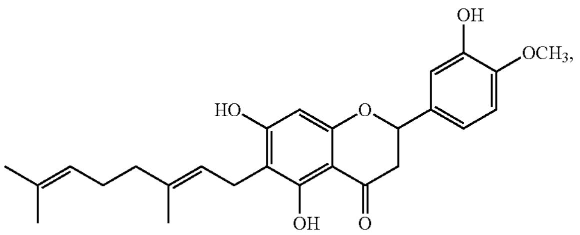

[Formula 7]

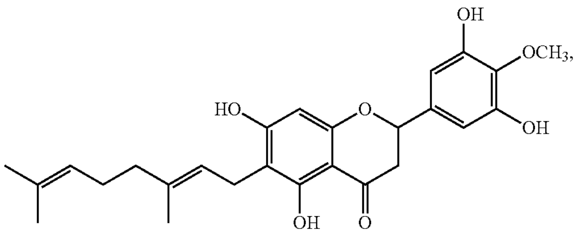

[Formula 8]

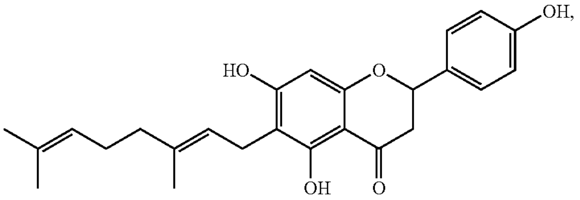

[Formula 9]

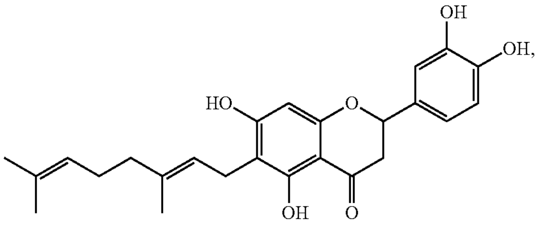

and

-continued

[Formula 10]

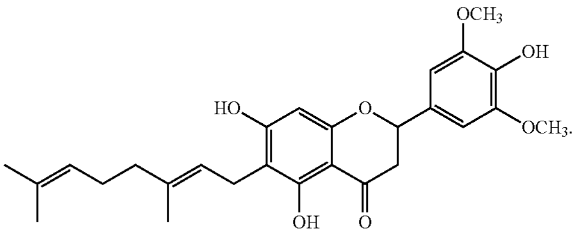

The present invention provides a use of a compound represented by Formula 1 or a pharmaceutically acceptable salt thereof for a health food for improving neuraminidase inhibition activity.

[Formula 1]

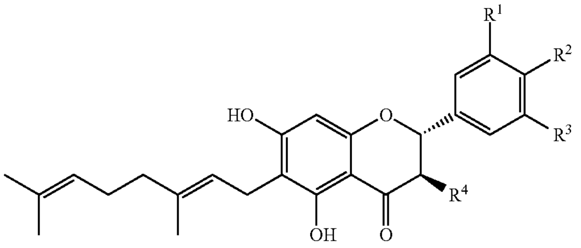

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

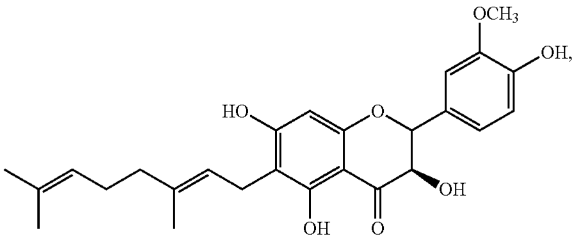

[Formula 3]

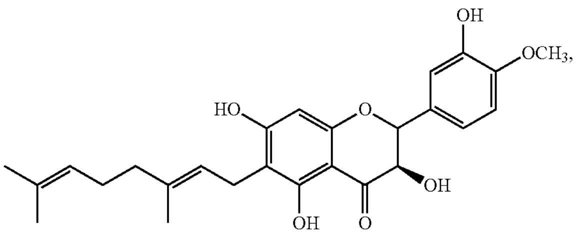

-continued

[Formula 4]

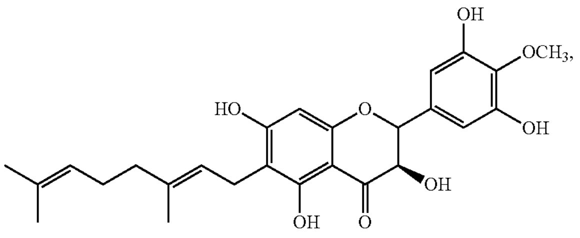

[Formula 5]

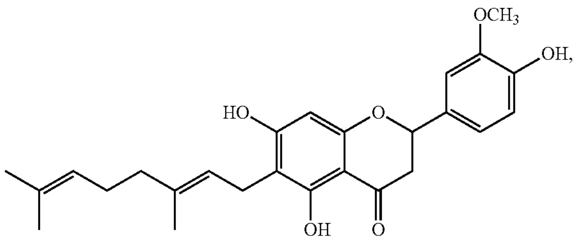

[Formula 6]

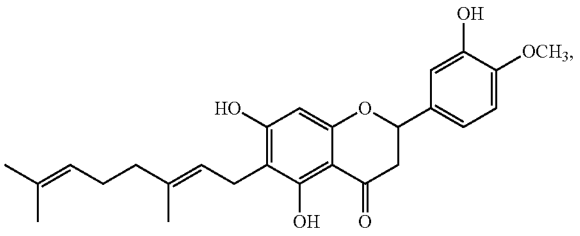

[Formula 7]

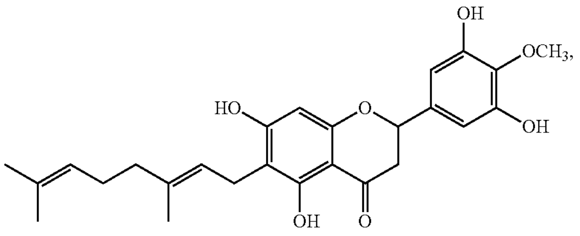

[Formula 8]

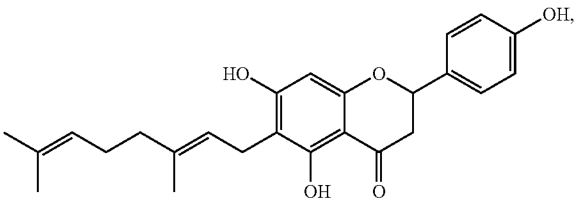

[Formula 9]

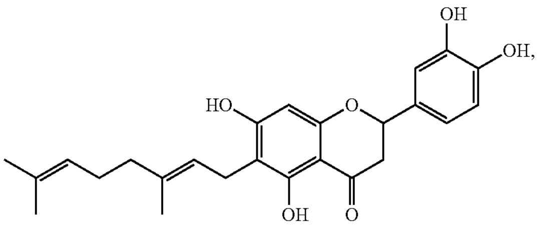

and

-continued

[Formula 10]

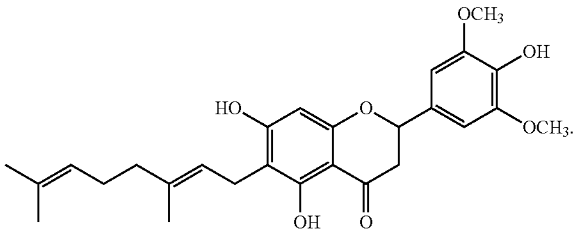

Further, the present invention provides a pharmaceutical composition for treating viral or bacterial inflammatory diseases, containing: an extract of *Paulownia tomentosa* or a fraction thereof as an active ingredient.

Further, the present invention provides a health food composition for treating viral or bacterial inflammatory diseases, containing: an extract of *Paulownia tomentosa* or a fraction thereof as an active ingredient.

Further, the present invention provides a pharmaceutical composition for treating viral or bacterial inflammatory diseases, containing: a pharmaceutically effective amount of a compound represented by Formula 1 or a pharmaceutically acceptable salt thereof as an active ingredient.

[Formula 1]

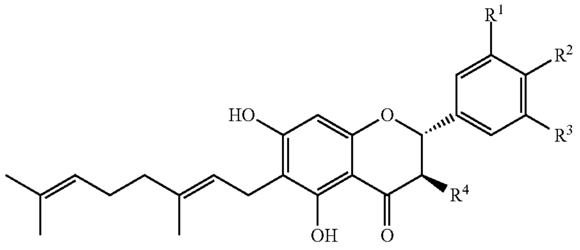

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

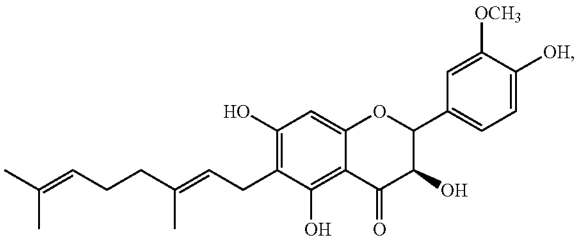

-continued

[Formula 3]

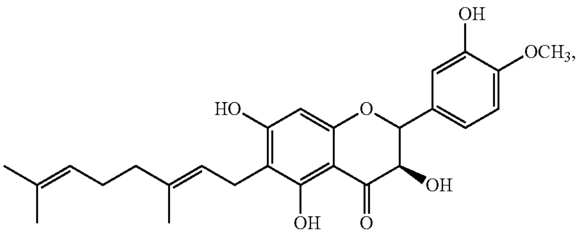

[Formula 4]

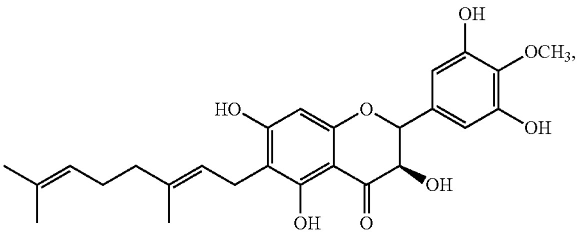

[Formula 5]

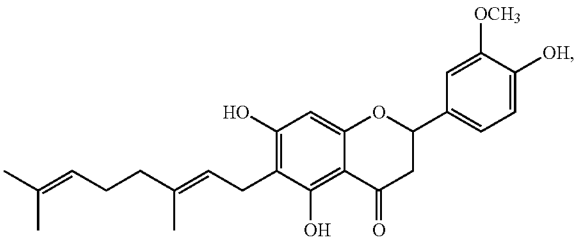 [SMILES: CC(C)=CCC/C(C)=C/Cc1c(O)cc2c(c1O)C(=O)CC(c1ccc(O)cc1)O2]

[Formula 6]

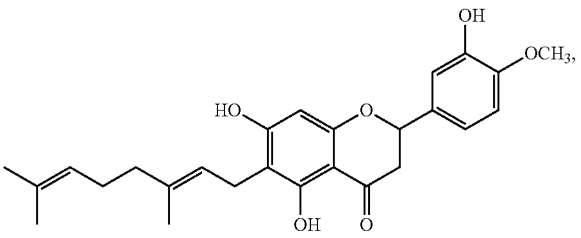

[Formula 7]

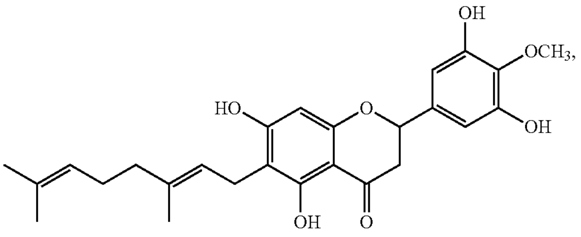

[Formula 8]

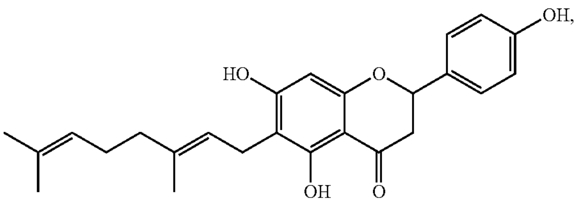

-continued

[Formula 9]

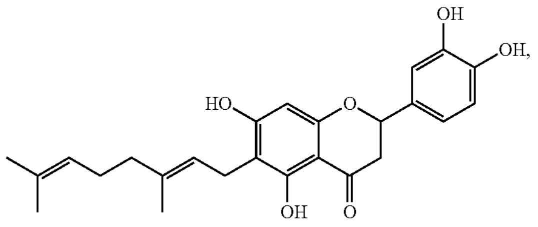

and

[Formula 10]

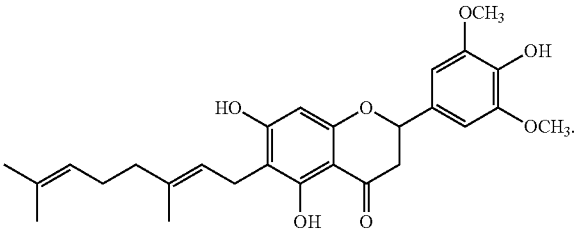

Further, the present invention provides a health food composition for treating viral or bacterial inflammatory diseases, containing: a pharmaceutically effective amount of a compound represented by Formula 1 or a pharmaceutically acceptable salt thereof as an active ingredient.

[Formula 1]

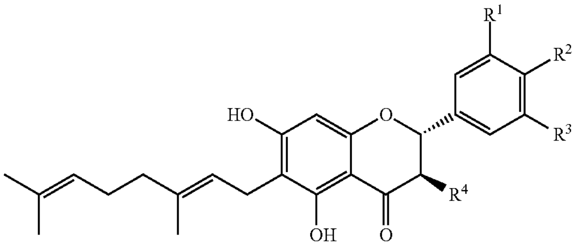

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

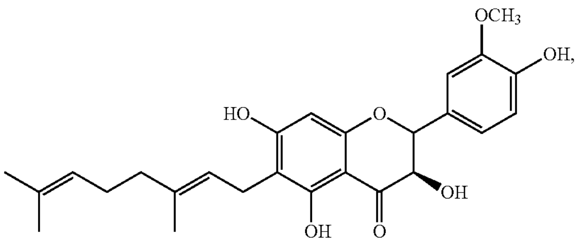

-continued

[Formula 3]

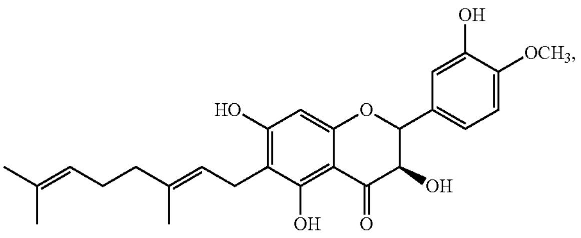

[Formula 4]

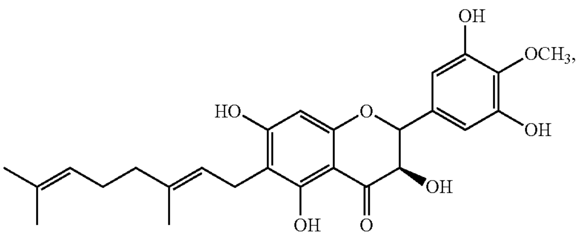

[Formula 5]

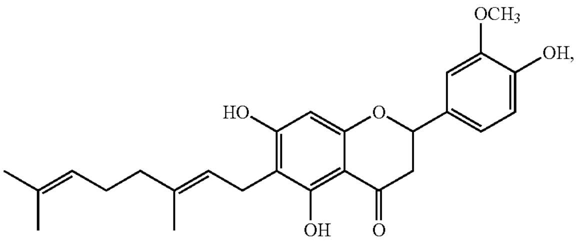

[Formula 6]

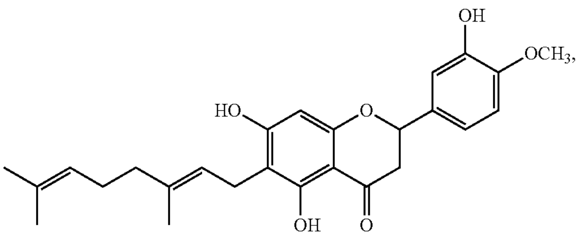

[Formula 7]

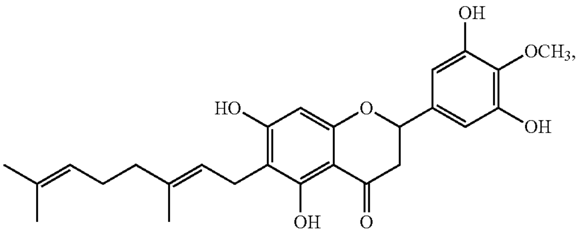

[Formula 8]

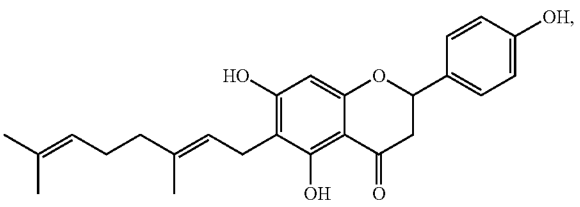

-continued

[Formula 9]

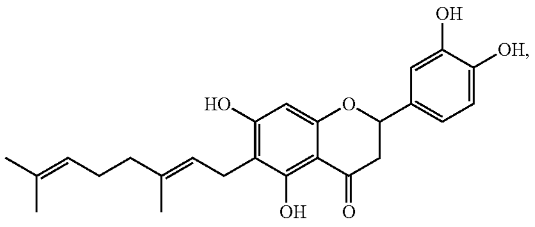

and

[Formula 10]

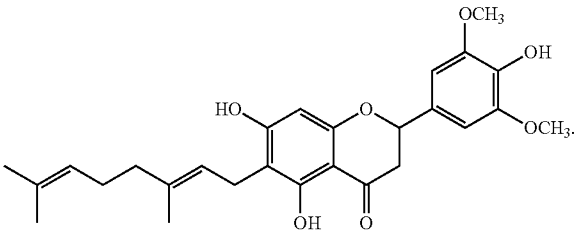

Further, the present invention provides a method for treating viral or bacterial inflammatory diseases by using an extract of *Paulownia tomentosa* or a fraction thereof as an active ingredient.

Further, the present invention provides a method for treating viral or bacterial inflammatory diseases by using a compound represented by Formula 1 or a pharmaceutically acceptable salt thereof as an active ingredient.

[Formula 1]

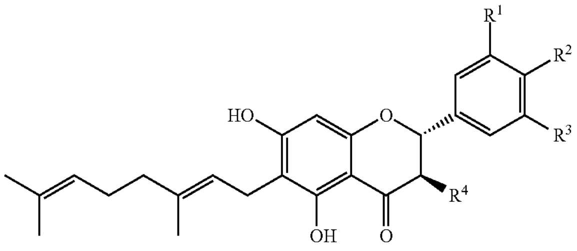

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

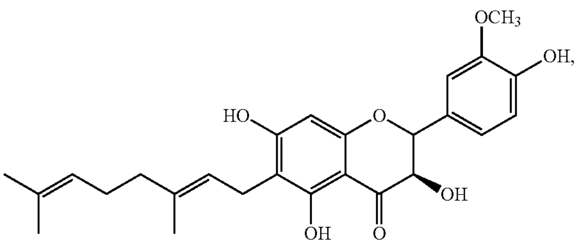

-continued

[Formula 3]

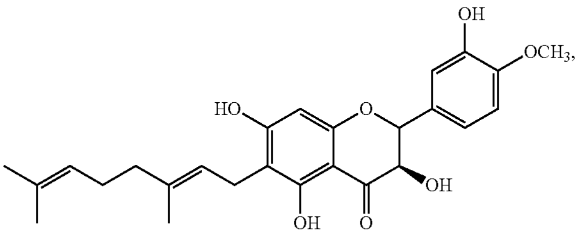

[Formula 4]

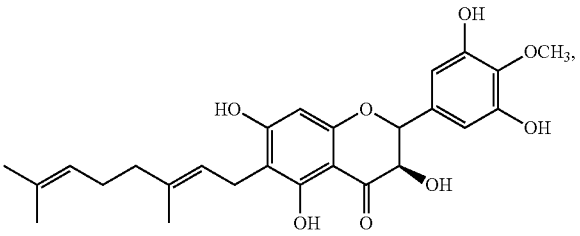

[Formula 5]

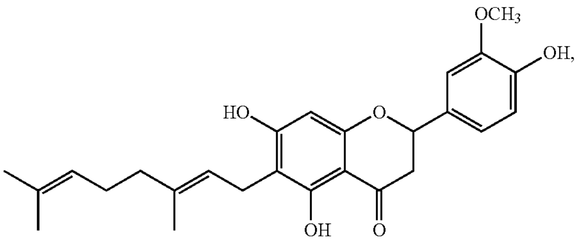

[Formula 6]

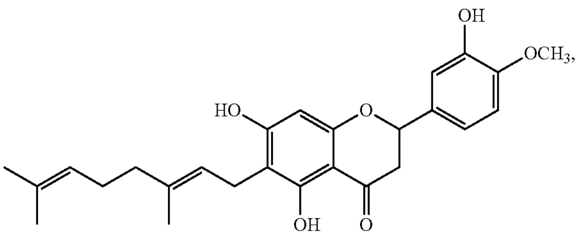

[Formula 7]

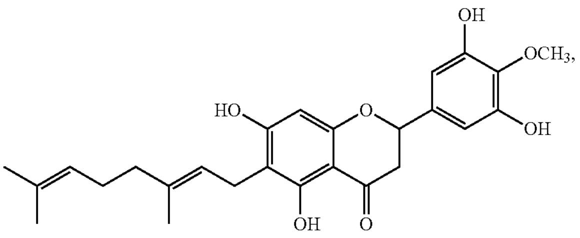

[Formula 8]

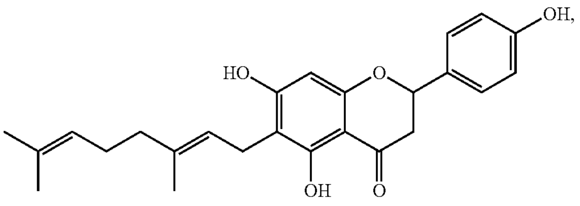

-continued

[Formula 9]

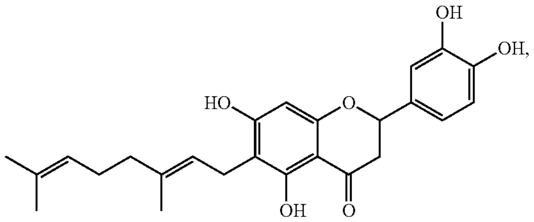

and

[Formula 10]

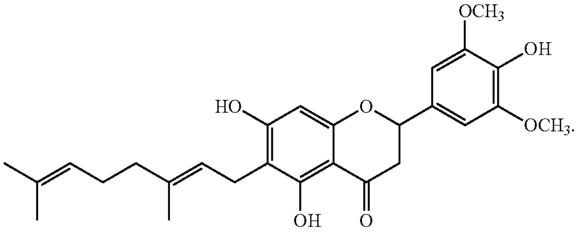

Further, the present invention provides a use of an extract of *Paulownia tomentosa* or a fraction thereof for a pharmaceutical composition for treating viral or bacterial inflammatory diseases.

Further, the present invention provides a use of an extract of *Paulownia tomentosa* or a fraction thereof for a health food for treating viral or bacterial inflammatory diseases.

Further, the present invention provides a use of a compound represented by Formula 1 or a pharmaceutically acceptable salt thereof for a pharmaceutical composition for treating viral or bacterial inflammatory diseases

[Formula 1]

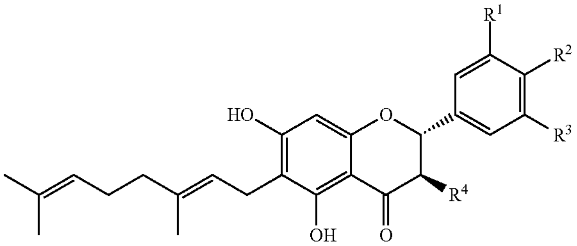

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

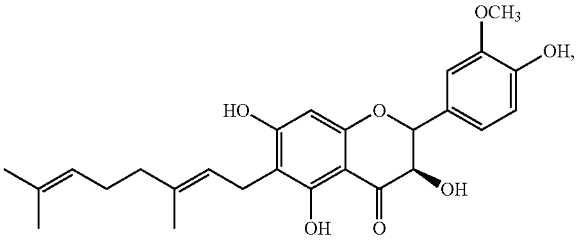

-continued

[Formula 3]

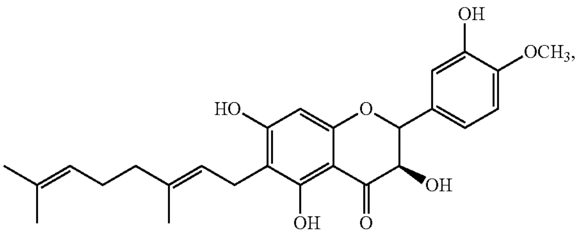

[Formula 4]

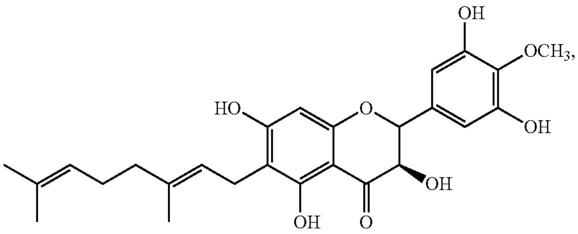

[Formula 5]

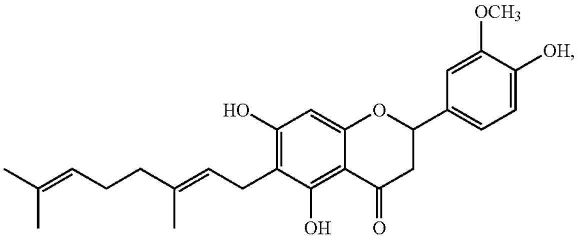

[Formula 6]

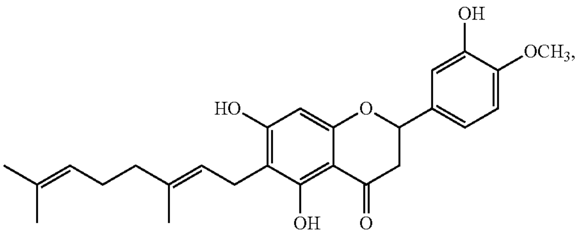

[Formula 7]

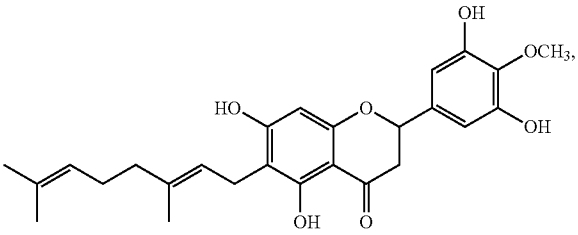

[Formula 8]

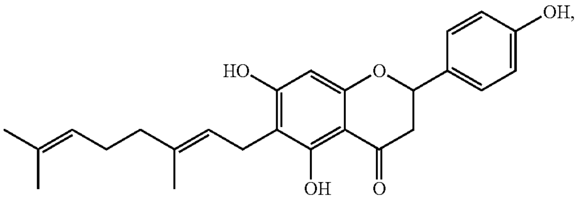

-continued

[Formula 9]

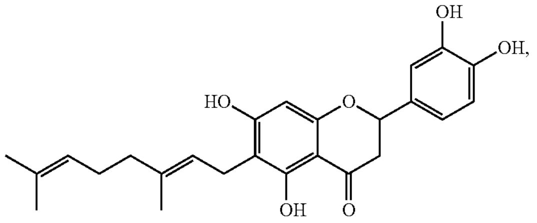

and

[Formula 10]

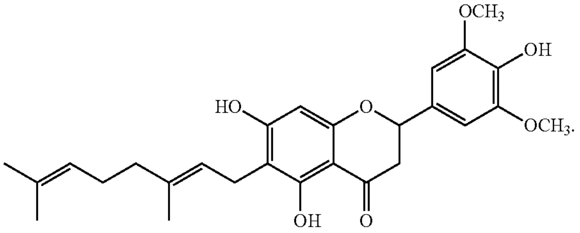

In addition, the present invention provides a use of a compound represented by Formula 1 or a pharmaceutically acceptable salt thereof for a health food for treating viral or bacterial inflammatory diseases.

[Formula 1]

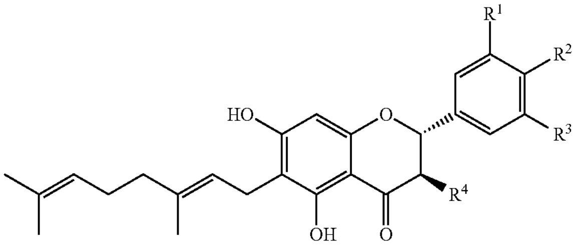

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

The compound represented by Formula 1 may be selected from the group consisting of compounds of Formulae 2 to 10:

[Formula 2]

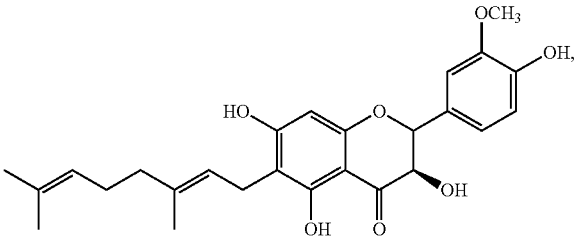

-continued

[Formula 3]

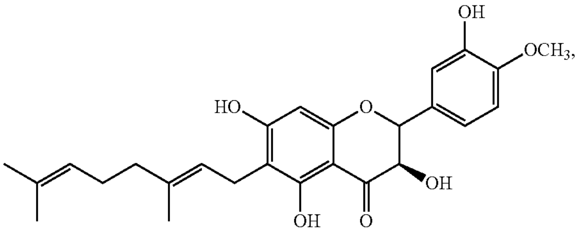

[Formula 4]

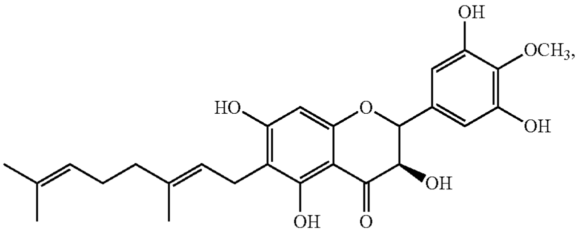

[Formula 5]

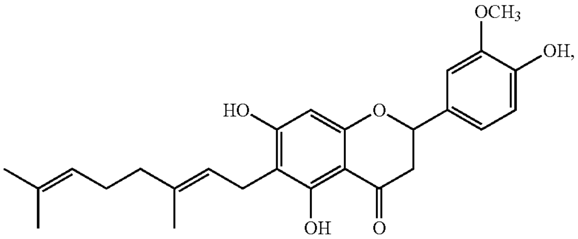

[Formula 6]

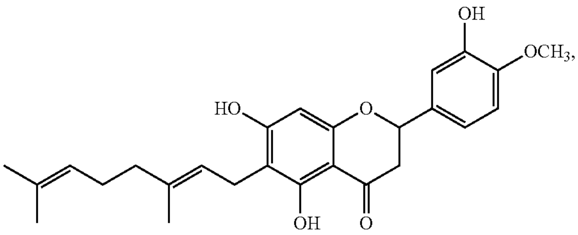

[Formula 7]

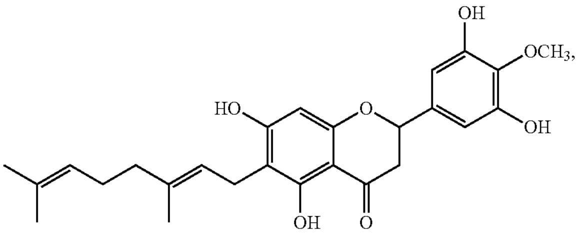

[Formula 8]

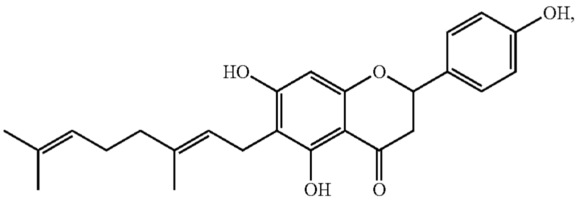

-continued

[Formula 9]

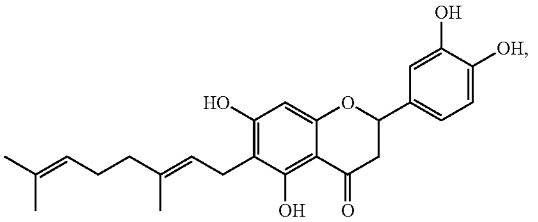

and

[Formula 10]

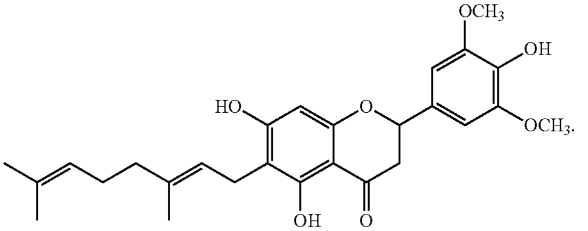

.

MODE FOR INVENTION

Hereinafter, the present invention will be described in more detail with reference to the following examples. It should be understood that these examples are provided for illustrative purposes only and are not to be in any way construed as limiting the present invention.

<Example 1> Preparation of Extract of *Paulownia tomentosa*

In order to prepare an extract of *Paulownia tomentosa,* 1 kg of fruits of *Paulownia tomentosa* dried in the shade (Jinju, Korea) were crushed and subjected to extraction at room temperature using 5 liters of methanol for 3 times. The methanolic extract of *Paulownia tomentosa* obtained by the above procedure was concentrated under reduced pressure to yield 118 g of a dark brown crude extract (yield rate: 11.8%).

<Example 2> Preparation of Fraction *Paulownia tomentosa*

118 g of the dark brown crude extract obtained in <Example 1> was dissolved in a mixed solvent consisting of distilled water and ethyl acetate, followed by fractionating ethyl acetate, and then drying the fractionated ethyl acetate over anhydrous $Na_2SO_4$ to yield 16 g of fractions.

<Example 3> Isolation and Purification of Novel Compounds from the Extract of *Paulownia tomentosa*

<3-1> Isolation and Purification of Geranylated Flavonoid Compounds

In order to isolate and purify flavonoids from the ethyl acetate fractions obtained by the method in <Example 2>, the ethyl acetate fractions were subjected to silica gel chromatography (200-400 mesh) using a mixed solvent (50:11:1) of hexane and ethyl acetate to yield 7 fractions (A-E).

Fraction A (4.2 g) was subjected to silica gel chromatography using a mixed solvent (100:11:1) of hexane and acetone to yield 9 fractions (A1-A9). Fractions A3 and A4 (460 mg) containing compounds 5 and 9 were subjected to a Sephadex LH-20 (Pharmacia Biotech AB, Uppsala, Sweden) using 80% methanol as a solvent to isolate compound 5 (25 mg) and compound 9 (18 mg). Fraction B (8.9 g) was subjected to silica gel chromatography using a mixed solvent (100:11:1) of chloroform and acetone to yield 10 fractions (B1-B10). Fractions B4 to B6 (512 mg) containing compounds 4 and 7 were subjected to silica gel chromatography using a mixed solvent (35:15:1) of hexane and acetone to isolate compound 4 (24 mg) and compound 7 (23.2 mg). Fraction C (1.8 g) was subjected to silica gel chromatography using a mixed solvent (50:11:1) of hexane and acetone to yield 9 fractions (C1-C9). Fractions C6 to C8 (362 mg) containing compounds 1 and 2 were subjected to reverse phase chromatography (ODS-A, 12 nm, S-150) using a mixed solvent (4:1) of methanol and water to isolate compound 1 (42 mg) and compound 2 (33.2 mg). Fraction D (13.1 g) was subjected to silica gel chromatography using a mixed solvent (50:11:1) of hexane and acetone to yield 25 fractions (D1-D25). Fractions D2 to D10 (613 mg) containing compounds 6 and 8 were subjected to reverse phase chromatography (ODS-A, 12 nm, 5-150) using a mixed solvent (4:1) of methanol and water to isolate compound 6 (21 mg) and compound 8 (19 mg). Fraction E (13.1 g) was subjected to silica gel chromatography using a mixed solvent (50:11:1) of hexane and acetone to yield 12 fractions (E1-E12). Fractions E3 to ES (308 mg) containing compound 3 were subjected to a Sephadex LH-20 (Pharmacia Biotech AB, Uppsala, Sweden) using 80% methanol as a solvent to isolate compound 3 (17 mg).

As a result, 9 geranylated flavonoid compounds, namely, 3'-O-methyldiplacol (compound 1, 42 mg), 4'-O-methyldiplacol (compound 2, 33.2 mg), 6-geranyl-3,3',5,5',7-pentahydroxy-4'-methoxyflavone (compound 3, 17 mg), 3'-O-methyldiplacone (compound 4, 24 mg), 4'-O-methyldiplacone (compound 5, 25 mg), 6-geranyl-3',5,5',7-tetrahroxy-4'-methoxyflavanone (compound 6, 21 mg), minulone (compound 7, 23.2 mg), diplacone (compound 8, 19 mg), and 6-geranyl-4',5,7-trihydroxy-3',5'-dimethoxyflavanone (compound 9, 18 mg) were isolated.

<3-2> Structure Analysis of Isolated Flavonoid

The structures of 9 flavonoid compounds isolated in <Example 3-1> were identified by nuclear magnetic resonance spectroscopy, mass spectroscopy, ultraviolet spectroscopy, polariscope and circular dichroism (CD) such as $^1H$ NMR (500 MHz), $^{13}C$ NMR (125 MHz), COSY, HMQC, HMQC, and HMBC. The results of compounds 1 to 9 are as follows.

Compound 1 [Formula 2]

(3'-O-methyldiplacol): $[\alpha]^{25}_D$-4 (c 5.4, $CHC_3$); UV (MeOH) $\lambda_{max}$ (log ε) 206, 295 nm; IR (KBr) $V_{max}$ 3745, 3456, 2923, 2853, 1635, 1458, 1120 $cm^{-1}$; mp>140° C.: $^1H$ NMR (500 MHz, acetone-$d_6$) δ 1.43 (3H, s, H-10"), 1.49 (3H, s, H-9"), 1.64 (3H, s, H-4"), 1.82 (2H, m, H-5"), 1.94 (2H, m, H-6"), 3.15 (2H, d, J=7.1 Hz, H-1"), 3.74 (3H, s, H-3'$OCH_3$), 4.53 (1H, d, J=11.6 Hz, H-3), 4.91 (1H, d, J=11.6 Hz, H-2), 4.95 (1H, t, H-7"), 5.12 (1H, t, H-2"), 5.91 (1H, s, H-6), 6.74 (1H, d, J=8.0 Hz, H-2'), 6.89 (1H, dd, J=1.7, 8.0 Hz, H-6'), 7.07 (1H, d, J=1.7 Hz, H-5'). $^{13}C$ NMR (125 MHz, acetone-$d_6$) 16.6 (C-4"), 18.1 (C-10"), 22.0 (C-1"), 26.2 (C-9"), 27.8 (C-6"), 40.9 (C-5"), 46.8 ($OCH_3$-3'), 80.8 (C-3), 85.1 (C-2), 96.0 (C-8), 105.8 (C-4a), 109.8 (C-6), 112.8 (C-5'), 115.8 (C-2'), 122.5 (C-6'), 123.8 (C-2"), 125.6 (C-7"), 130:2 (C-1'), 132.0 (C-8"), 135.6 (C-3"), 148.4 (C-4'), 148.6 (C-3'), 149.8 (C-8a), 162.2 (C-5), 165.9 (C-7), 198.6 (C═O, C-4): EIMS, m/z 454 $[M]^+$: HREIMS, m/z 454.1990 (calcd for $C_{26}H_{30}O_7$ 454.1992).

[Formula 2]

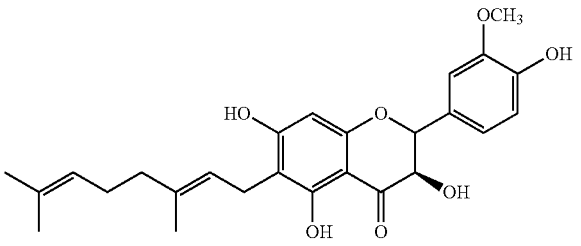

Compound 2 [Formula 3]

(4'-O-methyldiplacol): $[\alpha]^{25}{}_D$-4 (c 0.80, $CHCl_3$): UV (MEOH) $\lambda_{max}$ (log ε) 205, 295 nm: IR (KBr) $V_{max}$ 344.21, 2922.17, 1635.49 $cm^{-1}$; mp>140° C.; $^1$H NMR (500 MHz, $CD_3OD$) δ 1.46 (3H, s, H-10"), 1.52 (3H, s, H-9"), 1.67 (3H, s, H-4"), 1.84 (2H, m, H-5"), 1.94 (2H, m, H-6"), 3.11 (2H, d, J=7.1 Hz, H-1") 3.78 (3H, s, H-4'$OCH_3$), 4.41 (1H, d, J=10.8 Hz, H-3), 4.82 (1H, d, J=10.8 Hz, H-2), 5.10 (1H, t, H-7"), 5.12 (1H, t, H-2"), 5.75 (1H, s, H-8), 6.73 (10, d, J=8.1 Hz, H-5'), 6.85 (1H, dd, J=1.8, 8.1 Hz, H-6'), 7.00 (1H, d, J=1.8 Hz, H-2'). $^{13}$C NMR (125 MHz, $CD_3OD$) 18.7 (C-4"), 18.1 (C-9"), 22.3 (C-1"), 26.3 (C-10"), 28.2 (C-6"), 41.4 (C-5"), 56.9 ($OCH_3$-4'), 74.1 (C-3), 85.5 (0-2), 87.4 (C-8), 101.1 (C-4a), 111.1 (C-6), 112.8 (C-2'), 116.4 (0-5'), 122.5 (C-6'), 124.8 (C-2"), 126.0 (C-7"), 130.7 (C-1'), 132.4 (C-8"), 136.3 (C-3"), 148.7 (C-8a), 148.6 (C-3'), 149.3 (C-4'), 162.5 (C-8a), 162.6 (C-5), 162.7 (C-7), 197.4 (C═O, C-4); EIMS, m/z 454 $[M]^+$: HREIMS, m/z 454.1993 (calcd for $C_{26}H_{30}O_7$ 454.1992).

[Formula 3]

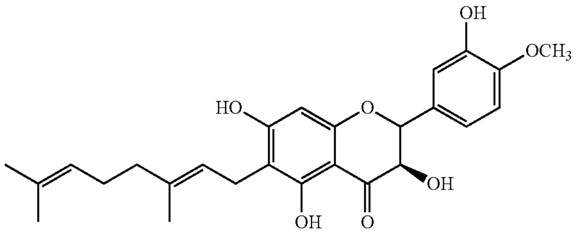

Compound 3 [Formula 4]

(6-geranyl-3,3',5,5',7-pentahydroxy-4'-methoxyflavane): $[\alpha]^{25}{}_D$-6 (c 0.74, $CHCl_3$); UV (MeOH) $\lambda_{max}$ (log ε) 206, 296 nm; IR (KBr) $V_{max}$ 3747, 3445, 2922, 2852, 1635, 1508, 1001, 1019 $cm^{-1}$; $^1$H NMR (500 MHz, acetone-$d_6$)

1.44 (3H, H-10"), 1.49 (3H, s, H-9"), 1.64 (3H, s, H-4"), 1.83 (2H, m, H-6'), 1.92 (2H, m, H-5"), 3.15 (2H, d, J=7.1H-1"), 3.71 (3H, s, H-4'$OCH_3$), 4.49 (1H, d, J=11.4 Hz, H-3), 4.84 (1H, d, J=11.4 Hz, H-2), 4.96 (1H, t, H-7"), 5.13 (1H, t, H-2"), 5.91 (1H, s, H-8), 6.62 (1H, d, J=4.2 Hz, H-6'), 6.62 (1H, d, J=4.2 Hz, H-2'). $^{13}$C NMR (125 MHz, $CD_3OD$)

16.6 (C-4"), 18.1 (C-10"), 20.0 (C-1"), 26.2 (C-9"), 27.8 (C-6"), 40.9 (C-5"), 57.0 ($OCH_3$-4"), 73.7 (C-3), 85.3 (C-2), 96.0 (C-8), 101.8 (C-4a), 104.9 (C-6'), 109.8 (C-6), 110.2 (C-2'), 123.8 (C-2"), 125.6 (C-7"), 129.5 (C-1'), 132.0 (C-8"), 135.5 (C-4'), 135.7 (C-3"), 146.5 (C-5'), 149.2 (C-3'), 162.2 (C-8a), 162.4 (C-5), 165.9 (C-7), 198.6 (C═O, C-4); EIMS, m/z 470 $[M]^+$: HREIMS, m/z 470.1942 (calcd for $C_{26}H_{30}O_7$ 454.1991).

[Formula 4]

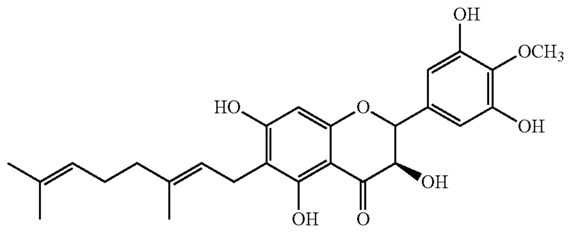

Compound 4 [Formula 5]

(3'-O-methyldiplacone): $[\alpha]^{25}{}_D$-17 (c 0.70, $CHCl_3$): UV (MeOH) $\lambda_{max}$ (log ε) 202, 204, 220, 286 nm: IR (KBr) $V_{max}$ 3863, 3785, 3446, 2923, 2852, 1835, 1457 $cm^{-1}$; mp>103° C. $^1$H NMR (500 MHz, $CD_3OD$) δ 1.47 (38, s, H-10"), 1.53 (3H, s, H-9"), 1.65 (3H, s, H-4"), 1.84 (2H, m, H-5"), 1.96 (2H, m. H-6"), 2.45 (1H, dd, J=3.1, 17.0 Hz, H-3b), 2.65 (1H, dd. J=12.5, 17.0 Hz, H-3a), 3.08 (28, d, J=6.9 Hz, H-1"), 3.77 (3H, s, H-3' $OCH_3$), 4.99 (1H, t, H-7"), 5.08 (1H, dd, J=3.1, 12.5 Hz, H-2), 5.14 (1H, t, H-2"), 5.62 (1H, s, H-8), 6.69 d, J=8.0 Hz, H-5'), 6.78 (1H, dd, J=1.8, 8.0 Hz, H-8'), 6.94 (1H, d, J=1.8 Hz, H-2'). $^{13}$C NMR (125 MHz, $CD_3OD$) 16.7 (C-4"), 18.1 (C-10"), 22.6 (C-1"), 26.3 (C-9"), 28.3 (C-6"), 41.5 (C-5"), 44.5 (C-3), 56.8 ($OCH_3$-3'), 80.4 (C-2), 100.2 (C-8), 100.7 (C-4a), 111.5 (C-2'), 112.2 (C-6), 116.7 (C-5'), 120.7 (C-6'), 126.2 (C-2"), 126.2 (C-7"), 132.2 (C-8"), 132.8 (C-1'), 134.2 (C-3"), 149.7 (C-3'), 161.3 (C-4'), 162.9 (C-8a), 163.1 (C-5), 179.8 (C-7), 194.0 (C═O, C-4): EIMS, m/z 438 $[M]^+$; HREIMS, m/z 438.2036 (calcd for $C_{26}H_{30}O_6$ 438.2042).

[Formula 5]

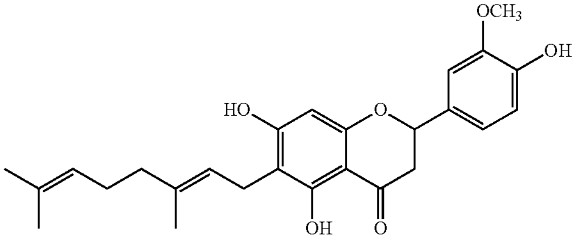

Compound 5 [Formula 6]

(4'-O-methyldiplacone): $[\alpha]^{25}{}_D$-17 (c 0.68, $CHCl_3$): UV (MeOH) $\Delta_{max}$ (log ε) 233, 292 nm: IR (KBr) $V_{max}$ 3455, 2920, 2851, 1635, 1456, 1384, 1273, 1159 $cm^{-1}$: mp>102° C.: $^1$H NMR (500 MHz, acetone-$d_6$) δ 1.58 (3H, s, H-10"), 1.64 (3H, s, H-9"), 1.79 (3H, s, H-4"), 1.98 (2H, m, H-5"), 2.07 (2H, m, H-6"), 2.74 (1H, dd, J=3.0, 17.1 Hz, H-3b), 3.18 (1H, dd, J=13.0, 17.1 Hz, H-3a), 3.30 (2H, d, J=7.2 Hz, H-1"), 3.90 (3H, s, H-4' $OCH_3$), 5.10 (1H, t, H-7"), 5.29 (1H, t, H-2"), 5.41 (1H, dd, J=2.8, 13.0 MHz, H-2), 6.07 (1H, s, H-8), 6.89 (1H, d, J=8.1 Hz, H-5'), 7.00 (1H, dd, J=1.9, 8.1 Hz, H-6'), 7.18 (1H, d, J=1.8 Hz, H-2'). $^{13}$C NMR (125 MHz, acetone-$d_6$) 16.7 (C-4"), 18.2 (C-10"), 22.0 (C-1"), 26.3 (C-9"), 27.9 (C-6"), 40.9 (C-5"), 44.3 (C-3), 56.8 ($OCH_3$-4'), 80.6 (C-2), 95.8 (C-8), 103.6 (C-4a), 109.5 (C-6), 111.6 (C-2'), 116.1 (C-5'), 120.9 (C-6'), 123.9 (C-2"), 125.6 (C-7"), 131.9 (C-8"), 132.0 (C-1'), 135.5 (C-3"), 148.3 (C-3'), 148.8 (C-4'), 162.4 (C-8a), 162.8 (C-5), 165.2 (C-7), 197.7 (C═O, C-4): EIMS, m/z 438 $[M]^+$; HREIMS, m/z 438.2040 (calcd for $C_{26}H_{30}O_6$ 438.2042).

[Formula 6]

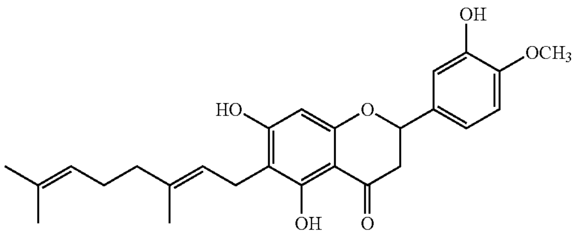

Compound 6 [Formula 7]

(6-geranyl-3',5,5',7-tetrahydroxy-4'-methoxyflavanone): $[\alpha]^{25}_D$−12 (c 0.76, $CHCl_3$); UV (MeOH) $\lambda_{max}$ (log ε) 204, 293 nm: IR (KBr) $V_{max}$ 3446, 2924, 2853, 1636, 1456, 1091 $cm^{-1}$; mp>140° C.: $^1$H NO (500 MHz, acetone-$d_6$) δ 1.43 (3H, s, H-10"), 1.49 (3H, s, H-9"), 1.64 (3H, s, H-4"), 1.82 (2H, m, H-5"), 1.94 (2H, m, H-6"), 3.15 (2H, d, 1=7.1 Hz, H-1"), 3.74 (3H, s, H-3'$OCH_3$), 4.53 (1H, d, J=11.6 Hz, H-3), 4.91 (1H, d, J=11.6 Hz, H-2), 4.95 (1H, t, H-7"), 5.12 (1H, t, H-2"), 6.91 (1H, s, H-8), 6.74 (1H, d, J=8.0 Hz, H-2'), 6.89 (1H, dd, J=1.7, 8.0 Hz, H-6'), 7.07 (1H, d, J=1.7 Hz, H-5'). $^{13}$C NMR (125 MHz, acetone-$d_6$) 16.6 (C-4"), 18.1 (C-10"), 22.0 (C-1"), 26.2 (C-9"), 27.8 (C-6"), 40.9 (C-5"), 46.8, ($OCH_3$-3'), 80.8 (C-3), 85.1 (C-2), 96.0 (C-8), 105.8 (C-4a), 109.8 (C-6), 112.8 (C-5'), 115.8 (C-2'), 122.5 (0-6'), 123.8 (C-2"), 125.6 (C-7"), 130.2 (C-1'), 132.0 (C-8"), 135.6 (C-3"), 148.4 (C-4'), 148.6 (C-3'), 149.8 (C-8a), 162.2 (C-5), 165.9 (C-7), 198.6 (C═O, C-4); EIMS, m/z 454 $[M]^+$; HREIMS, m/z 454.1990 (calcd for $C_{28}H_{30}O_7$ 454.1992).

[Formula 7]

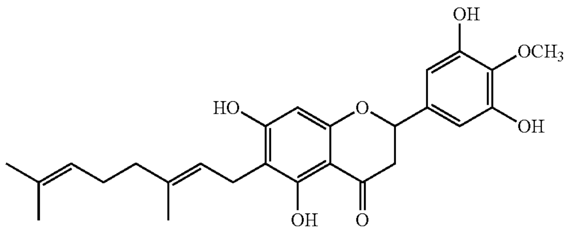

Compound 7 [Formula 8]

(mimulone): $[\alpha]^{25}_D$−1 (c 0.75, $CHCl_3$): UV (MeOH) $\lambda_{max}$ (log ε) 205, 296 nm; IR (KBr) $V_{max}$ 3901, 3745, 3673, 3649, 3445, 2924, 2853, 1736, 1636, 1540, 1508, 1457, 1091, 1019, 419 $cm^{-1}$; mp>116° C.; $^1$H NMR (500 MHz, $CDCl_3$) δ 1.52 (3H, s, H-10"), 1.60 (3H, s, H-9"), 1.73 (3H, s, H-4"), 1.99 (2H, m, H-5"), 2.02 (2H, m, H-6"), 2.70 (1H, dd, J=2.6, 17.1 Hz, H-3b), 3.00 (1H, dd, J=13.0, 17.1 Hz, H-3a), 3.26 (2H, d, J=7.0 Hz, H-1"), 5.18 (1H, t, H-2"), 5.24 (1H, dd, J=2.5, 13.0 Hz, H-2), 5.92 (1H, s, H-8), 6.79 (1H, s, H-5'), 6.80 (1H, s, H-3'), 7.22 (1H, s, H-6'), 7.24 (1H, s, H-2'). $^{13}$C NMR (125 MHz, $CDCl_3$) 16.6 (C-4"), 18.1 (C-10"), 21.5 (C-1"), 26.1 (C-9"), 26.8 (C-6"), 40.1 (C-5"), 43.6 (C-3), 79.2 (C-2), 96.1 (C-6), 103.3 (C-4a), 107.4 (C-8), 116.1 (C-3'), 116.1 (C-5'), 121.7 (C-2"), 124.1 (C-7"), 128.3 (C-2'), 128.3 (C-6'), 131.0 (C-1'), 132.5 (C-8"), 139.7 (C-3"), 156.6 (C-4'), 161.5 (C-8a), 161.7 (C-5), 164:5 (C-7), 196.7 (C═O, C-4): EIMS, m/z 408 $[M]^+$; HREIMS, m/z 408.1938 (calcd for $C_{25}H_{26}O_5$ 408.1937).

[Formula 8]

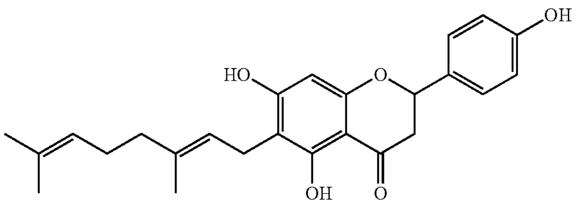

Compound 8 [Formula 9]

(diplacone): $[\alpha]^{25}_D$−8 (c 0.67, $CHCl_3$); UV (MeOH) $\lambda_{max}$ (log ε) 205, 292 nm; IR (KBr) $V_{max}$ 3673, 3445, 2924, 2853, 1736, 1636, 1457 $cm^{-1}$; mp>124° C.; $^1$H NMR (500 MHz, $CD_3OD$) δ 1.45 (3H, s, H-10"), 1.51 (3H, s, H-9"), 1.64 (3H, s, H-4"), 1.84 (2H, m, H-5"), 1.94 (2H, m, H-6"), 2.57 (1H, dd, J=2.8, 17.1 Hz, H-3b), 2.94 (1H, dd, J=12.8, 17.1 Hz, H-3a), 3.11 (2H, d, J=7.1 Hz, H-1"), 4.95 (1H, t, H-7"), 5.09 (1H, t, H-2"), 5.13 (1H, dd, J=2.7, 12.8 Hz, H-2), 5.83 (1H, s, H-8), 6.68 (2H, s, H-5', 6'), 6.81 (1H, s, H-2'). $^{13}$C NMR (125 MHz, $CD_3OD$) 16.8 (C-4"), 18.1 (C-10"), 22.2 (C-1"), 26.3 (C-9"), 28.2 (C-6"), 41.3 (C-5"), 44.7 (C-3), 80.9 (C-2), 95.9 (C-8), 103.6 (C-4a), 110.1 (C-6), 115.1 (C-2'), 116.7 (C-5'), 119.7 (C-6'), 124.4 (C-2"), 125.9 (C-7"), 132.4 (C-1'), 132.4 (C-8"), 135.7 (C-3"), 146.9 (C-3'), 147.3 (C-4'), 162.8 (C-8a), 162.9 (C-6), 166.4 (C-7), 198.2 (C═O, C-4); EIMS, m/z 424 $[M]^+$: HREIMS, m/z 424.1889 (calcd for $C_{25}H_{26}O_6$ 424.1886).

[Formula 9]

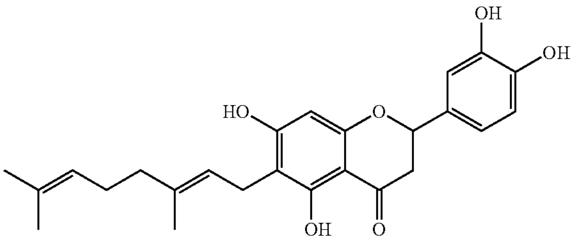

Compound 9 [Formula 10]

(6-geranyl-4',5,7-trihydroxy-3',5'-dimethoxyflavanone): $[\alpha]^{25}_D$−19 (c 0.74, $CHCl_3$): UV (MeOH) $\lambda_{max}$ (tog c) 205, 294 nm: IR (KBr) $V_{max}$ 3446, 2923, 2852, 1636, 1457, 1117 $cm^{-1}$: mp>78° C.: $^1$H NMR (500 MHz, acetone-$d_6$) δ 1.43 (3H, s, H-10"), 1.49 (3H, s, H-9"), 1.64 (3H, s, H-4"), 1.83 (2H, m, H-5"), 1.93 (2H, m, H-6"), 2.59 (1H, dd, J=2.8, 17.1 Hz, H-3b), 3.06 (1H, dd, J=13.0, 17.1 Hz, H-3a), 3.14 (2H, d, J=7.1 Hz, H-1"), 3.72 (3H, s, H-3' $OCH_3$), 3.72 (3H, s, H-5' $OCH_3$), 4.95 (1H, t, H-7"), 5.13 (1H, t, H-2"), 5.26 (1H, dd, J=2.8, 13.0, H-2), 5.93 (1H, s, H-8), 6.73 ($^1$H, s, H-2'), 6.73 (1H, s, H-6'). $^{13}$C NMR (125 MHz, acetone-$d_6$) 16.6 (C-4"), 18.1 (C-10"), 22.0 (C-1"), 26.2 (C-9"), 27.9 (C-6"), 40.9 (C-5"), 44.4 (C-3), 57.2 ($OCH_3$-3'), 57.2 ($OCH_3$-5'), 80.9 (C-2), 95.8 (C-8), 103.5 (C-4a), 105.8 (C-2'), 105.8 (C-6'), 109.5 (C-6), 123.8 (C-2"), 125.6 (C-7"), 130.2 (C-1'), 132.0 (C-6"), 135.5 (C-3"), 137.7 (C-4'), 149.2 (C-3'), 149.2 (C-5'), 162.4 (C-8a), 162.8 (C-5), 165.1 (C-7), 197.7 (C═O, C-4): EIMS m/z 342 $[M]^+$: EIMS, m/z 468 $[M]^+$; HREIMS, m/z 468.2151 (calcd for $C_{27}H_{32}O_7$ 468.2148).

[Formula 10]

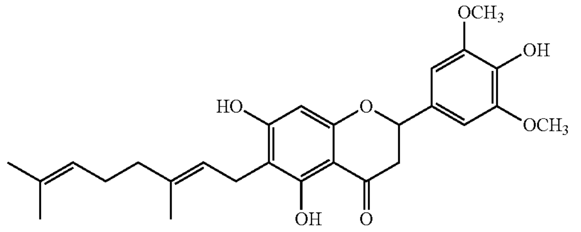

<Experimental Example 1> Identification of Neuraminidase Activity Inhibition

In order to identify neuraminidase inhibition effect of 9 flavonoid compounds isolated in <Example 3>, fluorescence analysis was performed. Neuraminidase of 33 family was an enzyme hydrolyzing α23 and α28 glycosidic linkages of sialic acid residues.

Specifically, in order to determine $IC_{50}$ of the compounds for neuraminidase, 0.01 U/ml of neuraminidase (EC. 3.2.1.8, *C. perfringens*, SIGMA, N2876) as an enzyme, 4-methylumbelliferyl-a-D-N-acetylneuraminic acid (SIGMA, M8639) mixed in 0.1 mM acetate buffer [50 mM sodium acetate (pH 5.0)] as a substrate, and inhibitors dissolved in methanol in each concentration were prepared. Fluorescence analysis was observed by SpectraMax M3 through excitation at 365 nm and emission at 450 nm (gain 40 nm). The activity analysis was performed on a 96 well plate (SPL Life Sciences, Korea) by providing total 200 μl of a solution comprising an enzyme (10 μl), a substrate (20 μl), an inhibitor (10 μl), and an acetate buffer (160 μl). By plotting initial rates of inhibition reactions occurring at different concentrations of inhibitors, the inhibition capability was evaluated. $IC_{50}$ values were calculated in accordance with the following Mathematical Formula 1:

$$vi = \frac{vo}{\left(1 + \frac{[I]}{IC_{50}}\right)}$$ [Mathematical Formula 1]

Figure 2:
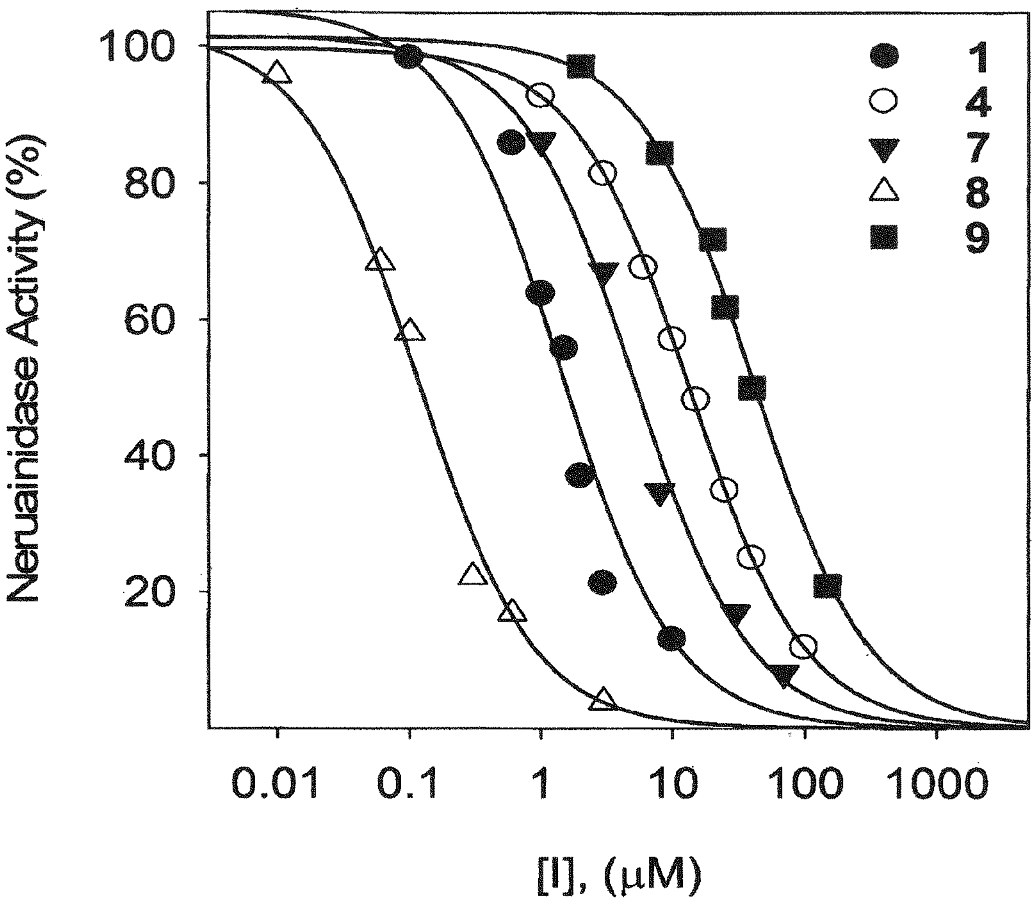
FIG. 2 shows neuraminidase inhibition activity of effective components (compounds 1 to 9) of an extract of *Paulownia tomentosa.*

As a result, as shown in Table 1, it was found that the geranylated flavonoid compounds (compounds 1-9) had high inhibition activity for neuraminidase. Compounds 1-3, 6 and 8 exhibited $IC_{50}$ values at nanomolar levels. Compound 8 having the best inhibition activity exhibited the lowest $IC_{50}$ values of 0.11±0.003. It was also found that other compounds significantly inhibited neuraminidase activity (Table 1). Further, as shown in Table 2, it was found that the geranylated flavonoid compounds (compounds 1-9) isolated from fruits of *Paulownia tomentosa* inhibited neuraminidase activity depending upon concentration (FIG. 2).

TABLE 1

| Compound | $IC_{50}$ (mM) | Kinetic measurement $K_i$ (mM) | Inhibition |
|---|---|---|---|
| Compound 1 | 1.6 ± 0.04 | 0.9 ± 0.02 | Competitive |
| Compound 2 | 1.4 ± 0.02 | 1.3 ± 0.03 | Competitive |
| Compound 3 | 0.38 ± 0.01 | 0.02 ± 0.12 | Competitive |
| Compound 4 | 14.3 ± 0.5 | 13.8 ± 2.3 | Competitive |
| Compound 5 | 12.9 ± 0.4 | 6.6 ± 0.3 | Competitive |
| Compound 6 | 0.19 ± 0.002 | 0.14 ± 0.02 | Competitive |
| Compound 7 | 6.1 ± 0.3 | 3.7 ± 0.4 | Competitive |
| Compound 8 | 0.11 ± 0.003 | 0.004 ± 0.001 | Competitive |
| Compound 9 | 38.4 ± 0.7 | 28.7 ± 0.4 | Competitive |

<Experimental Example 2> Analysis of Neuraminidase Inhibition Mechanism

In order to examine how the compounds of the present invention according to the results summarized in <Experimental Example 1> inhibit neuraminidase activity, Lineweaver-Burk and Dixon plots were created.

Specifically, based on results summarized in <Experimental Example 1>, the reactions occurring in the reaction mass of substrates and inhibitors in various concentrations were analyzed by fluorescence emitting values. Data analysis was performed using changes in fluorescence values as a slope for 20 minutes. The changes in fluorescence values were measured every 20 seconds and evaluated by Lineweaver-Burk and Dixon plots.

Figure 3:
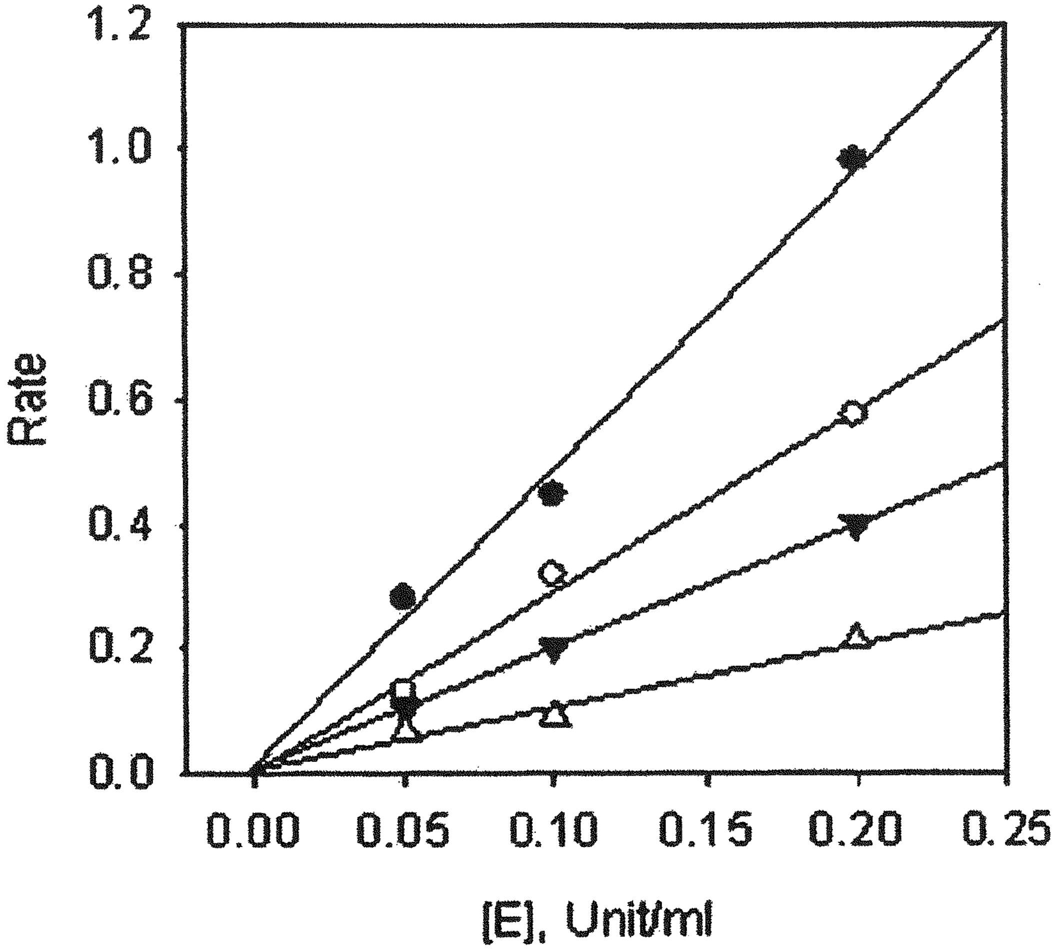
FIG. 3 shows a graph that depicts mechanisms of neuraminidase inhibition activity of effective components (compounds 1 to 9) of an extract of *Paulownia tomentosa* and defines compounds 1 to 9 as reversible enzyme inhibitors.

As a result, as shown in FIG. 3, each change in a test at different enzyme concentrations and inhibitor concentrations appears to be a straight line. Since each straight line is met at an identical intersection point, all the compounds were found to be reversible enzyme inhibitors (FIG. 3).

Figure 4:
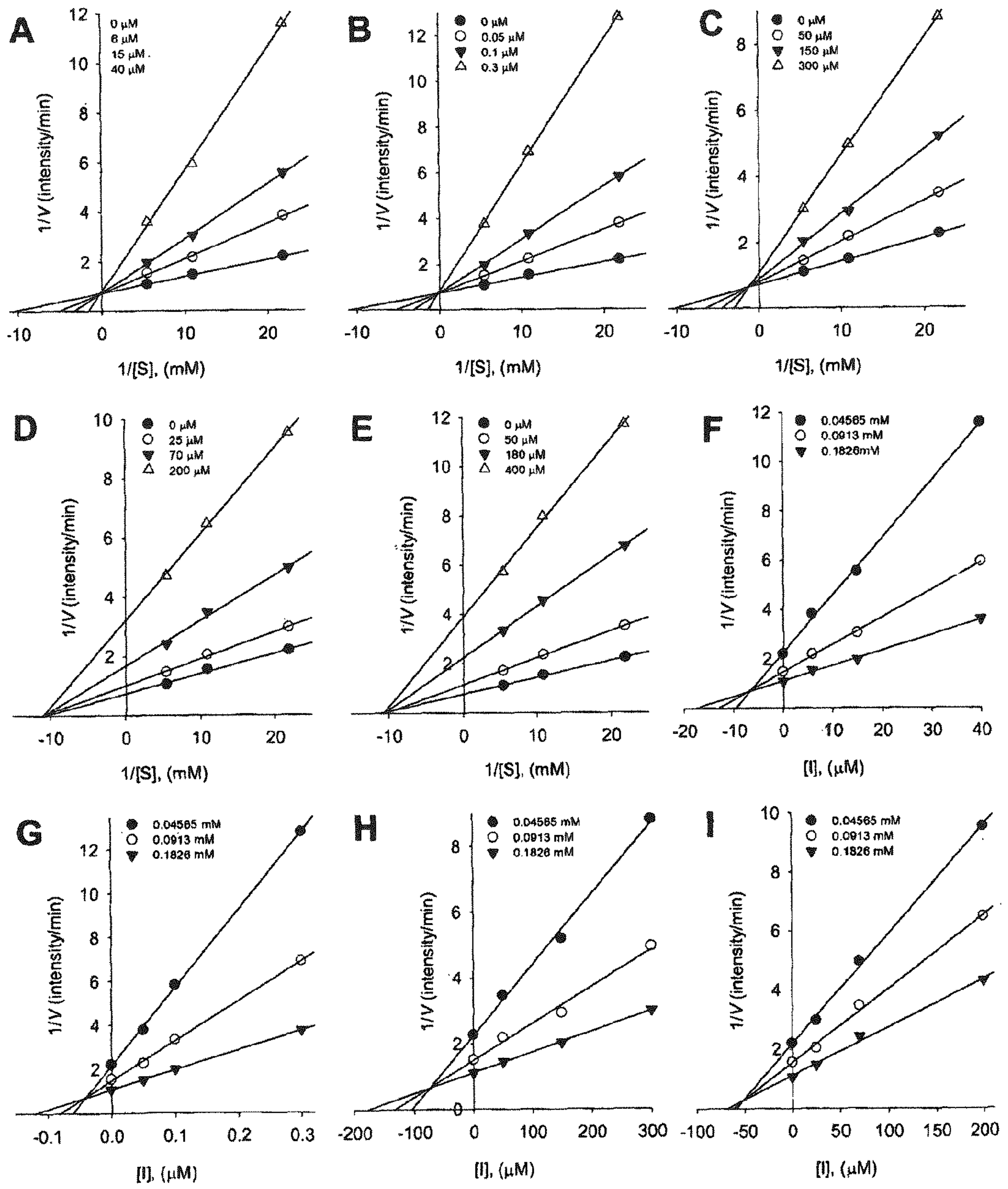
FIG. 4 shows a Lineweaver-Burk plot for neuraminidase inhibition activity of effective components (compounds 1 to 9) of an extract of *Paulownia tomentosa.*
Figure 5:
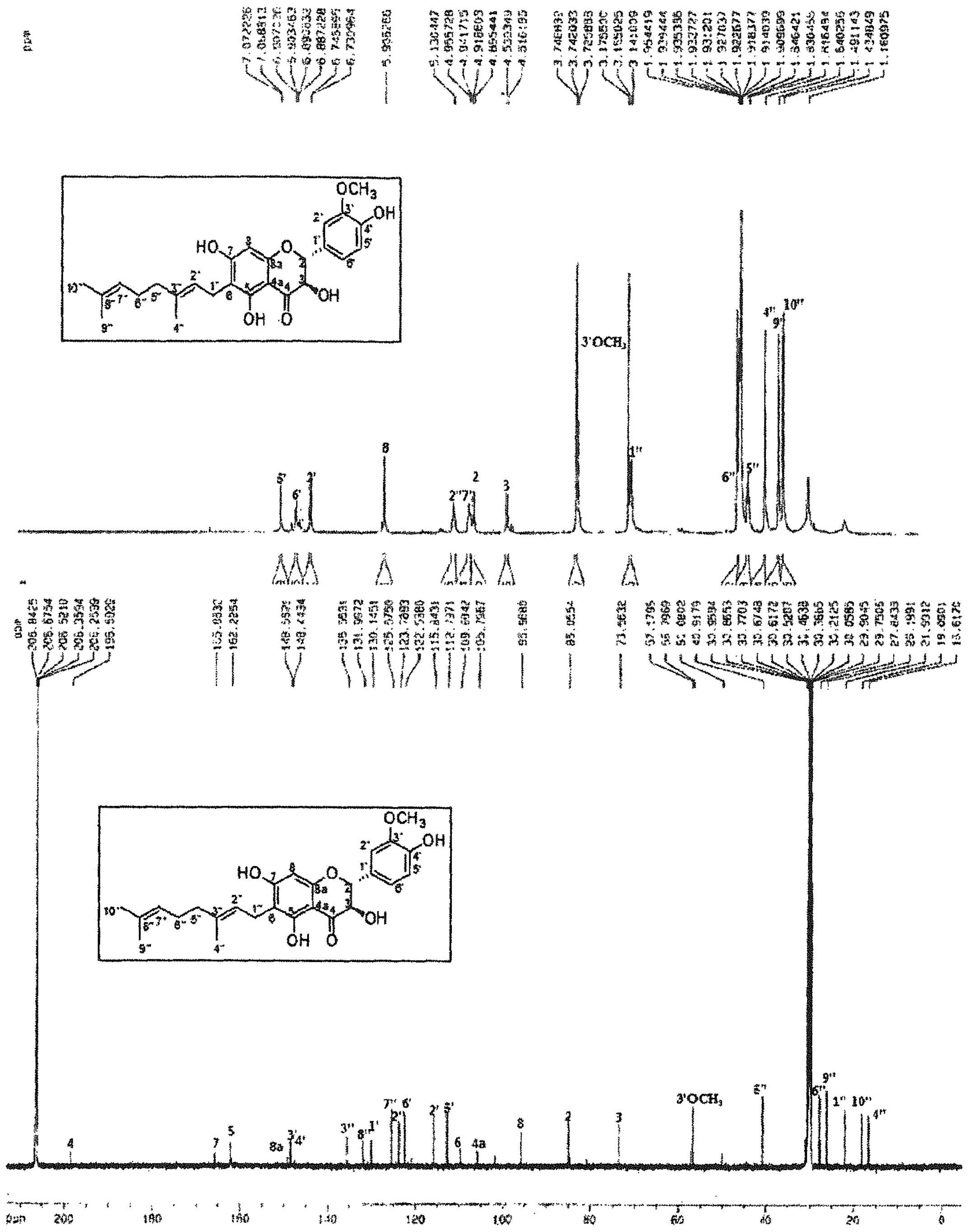
FIG. 5 shows $^{1}H$ and $^{13}C$-NMR results of an effective component (compound 1) of an extract of *Paulownia tomentosa.*
Figure 6:
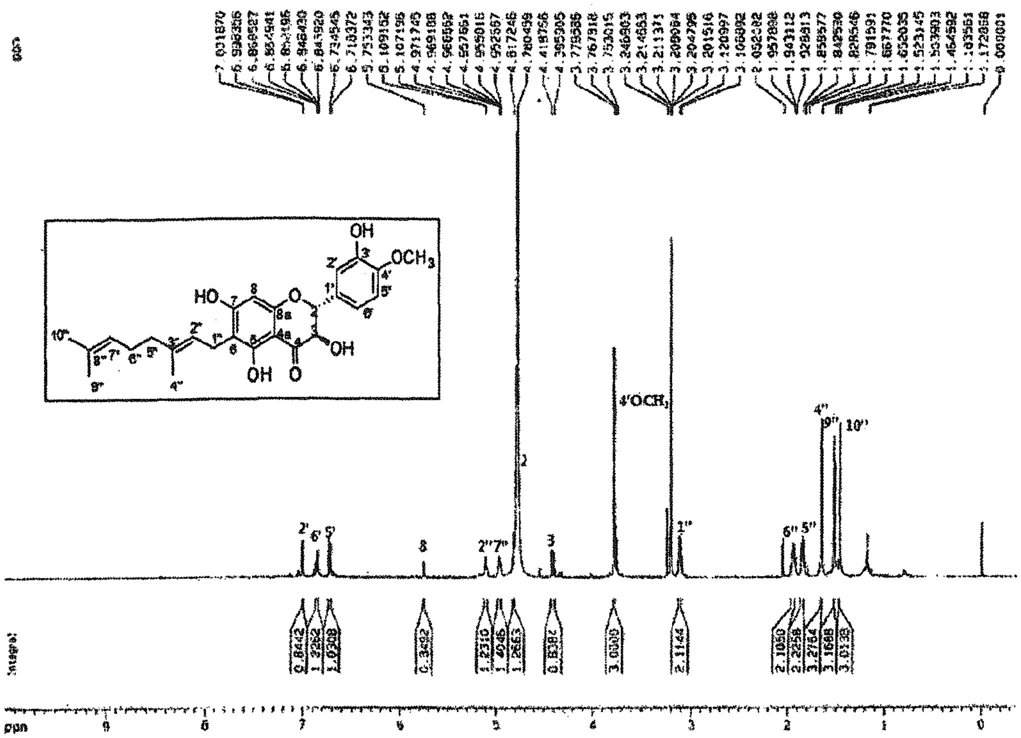
FIG. 6 shows $^{1}H$ and $^{13}C$-NMR results of an effective component (compound 2) of an extract of *Paulownia tomentosa.*
Figure 6:
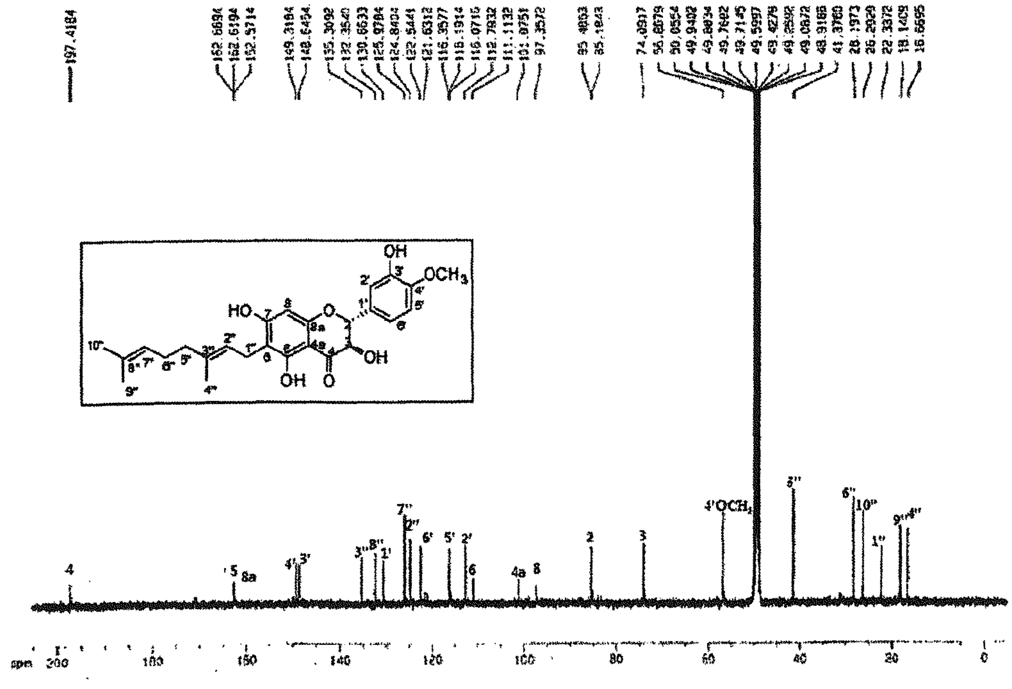
Figure 7:
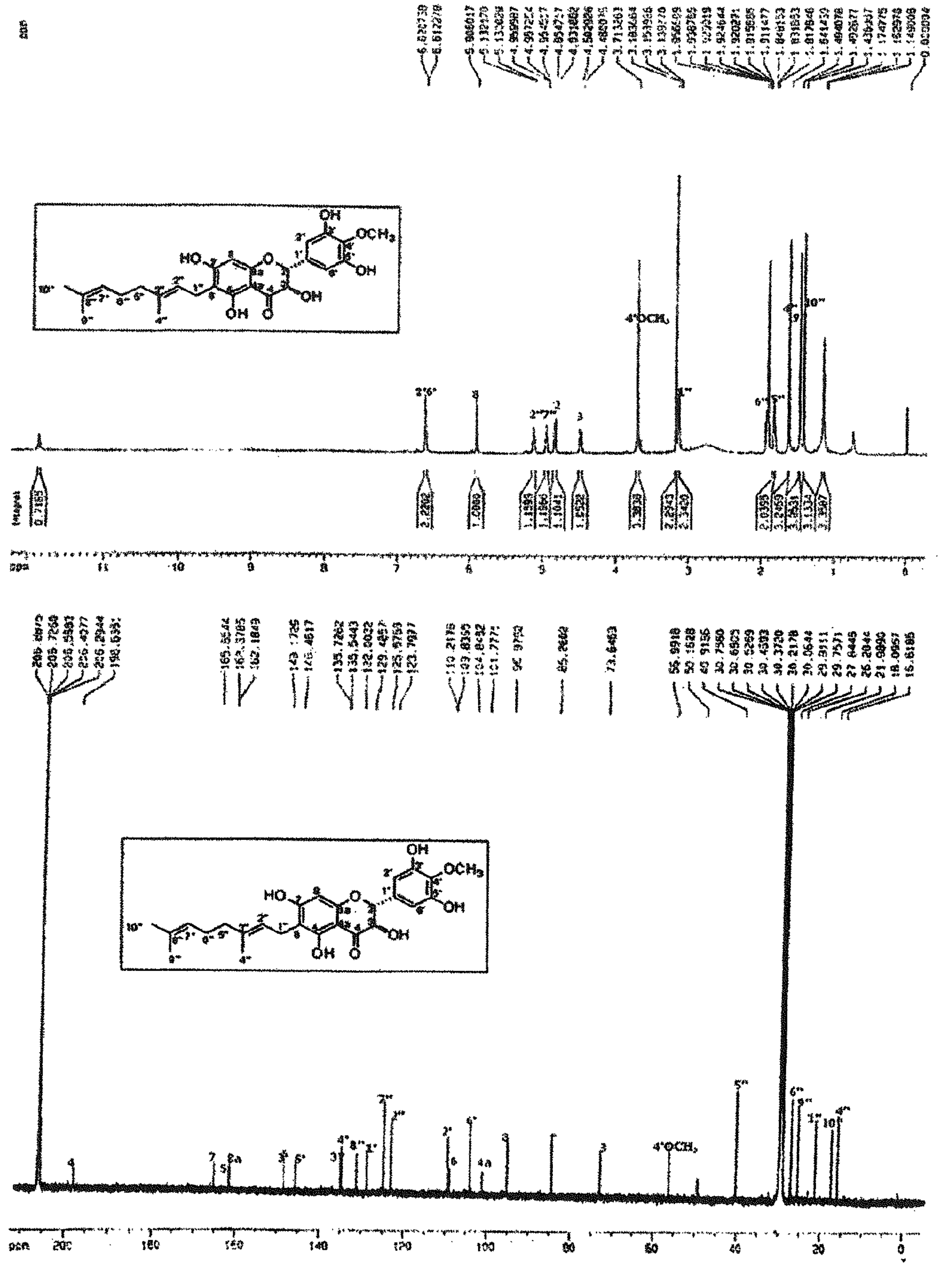
FIG. 7 shows $^{1}H$ and $^{13}C$-NMR results of an effective component (compound 3) of an extract of *Paulownia tomentosa.*
Figure 8:
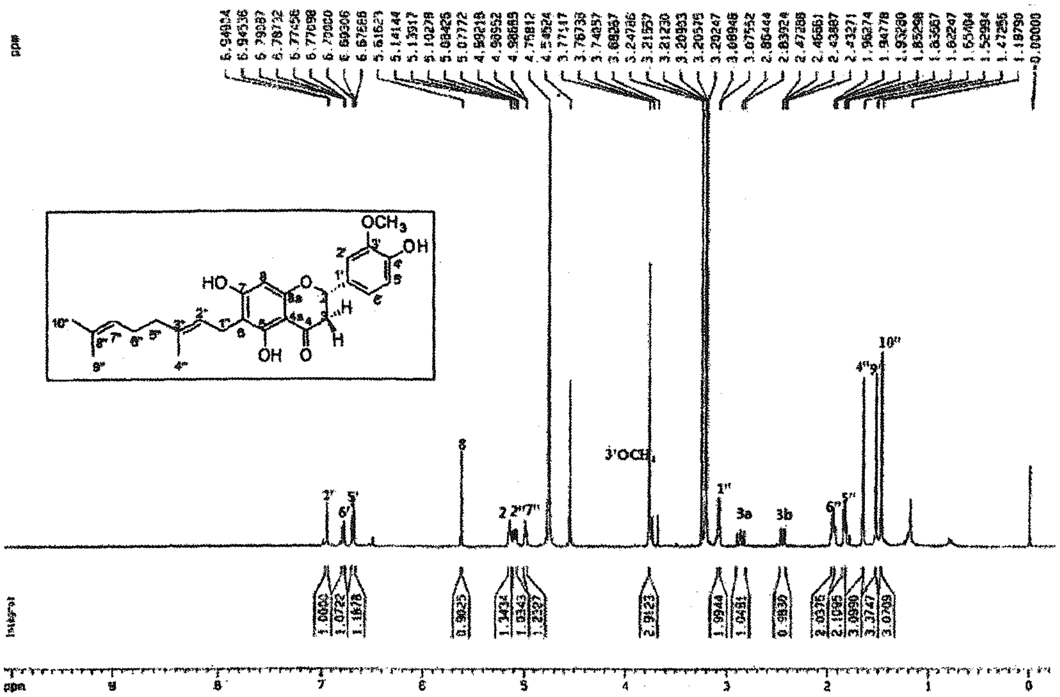
FIG. 8 shows $^{1}H$ and $^{13}C$-NMR results of an effective component (compound 4) of an extract of *Paulownia tomentosa.*
Figure 8:
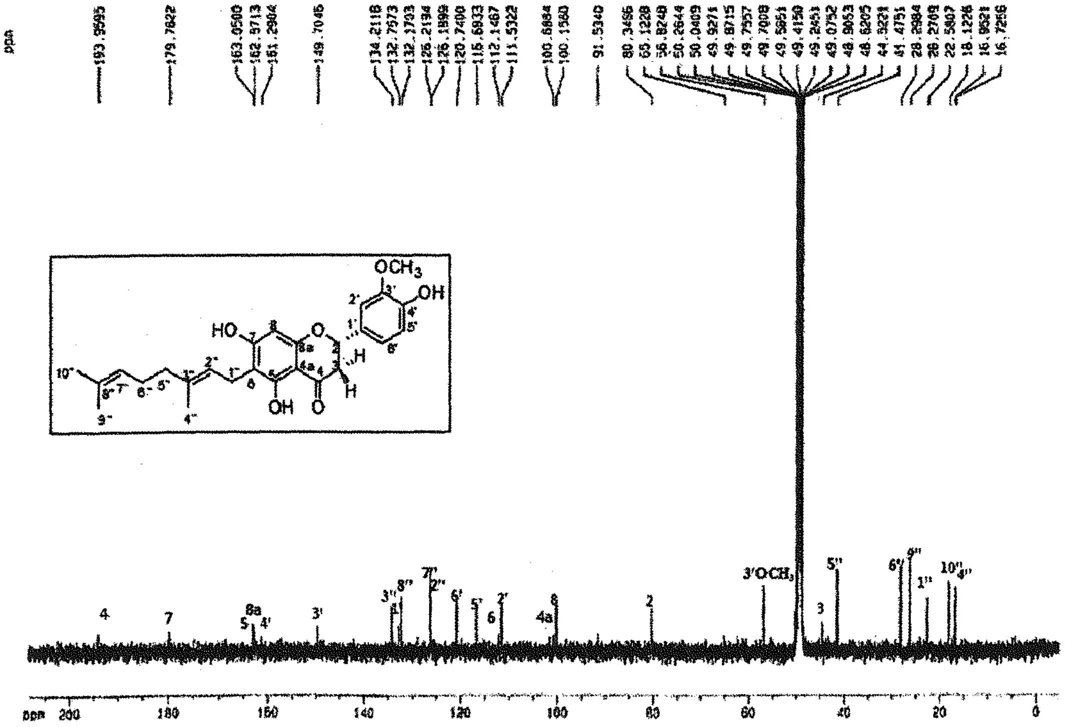
Figure 9:
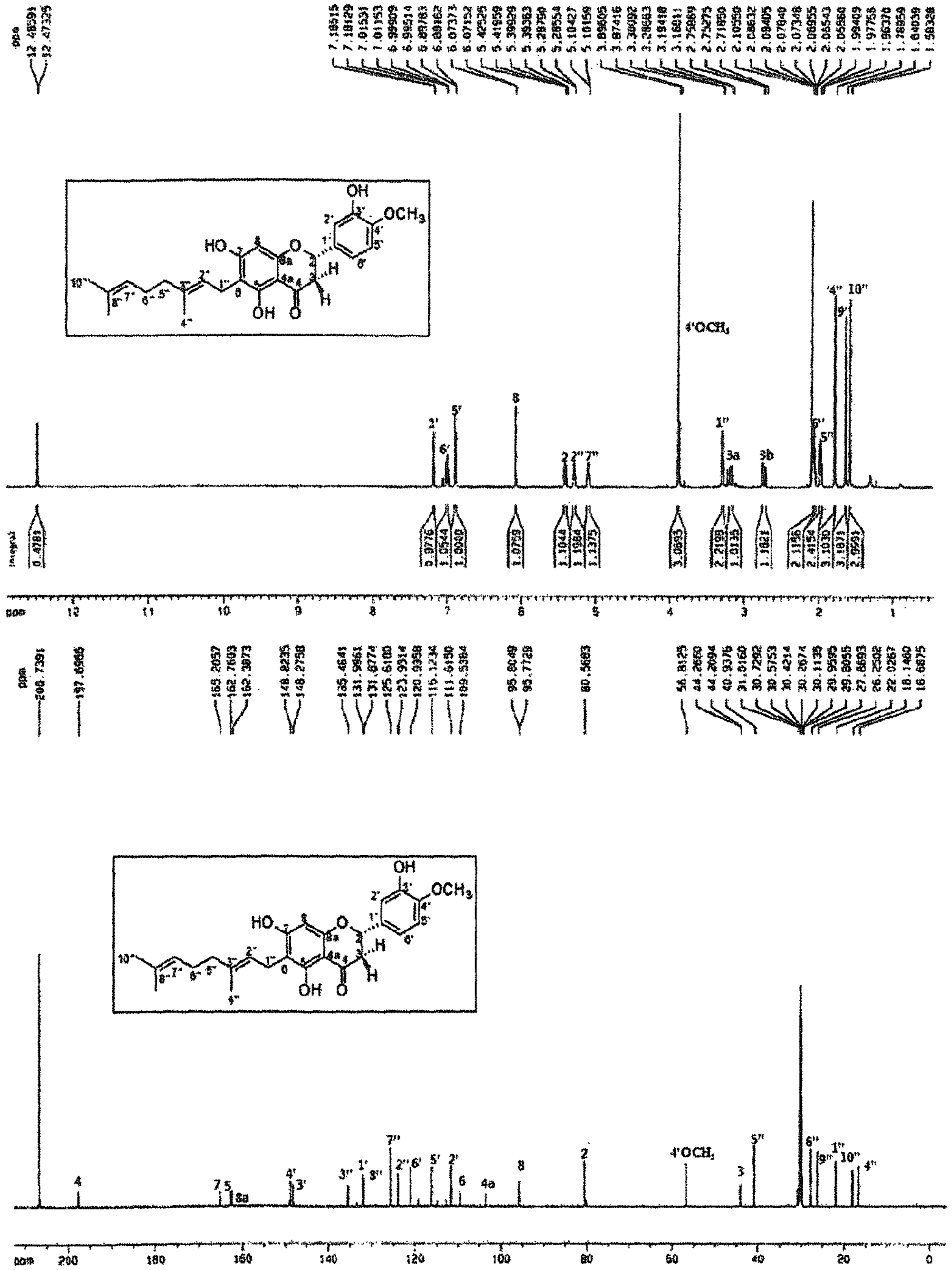
FIG. 9 shows $^{1}H$ and $^{13}C$-NMR results of an effective component (compound 5) of an extract of *Paulownia tomentosa.*
Figure 10:
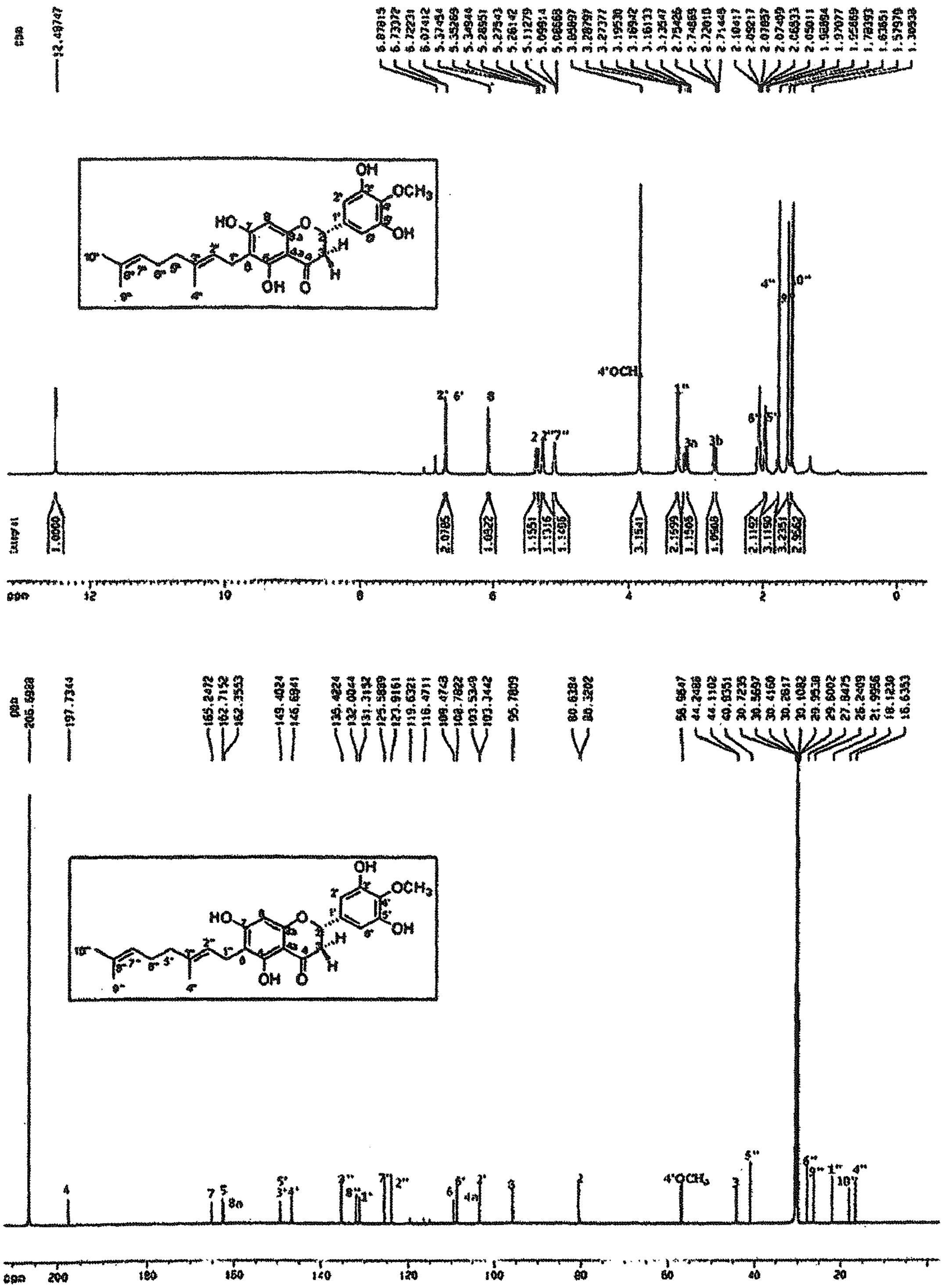
FIG. 10 shows $^{1}H$ and $^{13}C$-NMR results of an effective component (compound 6) of an extract of *Paulownia tomentosa.*
Figure 11:
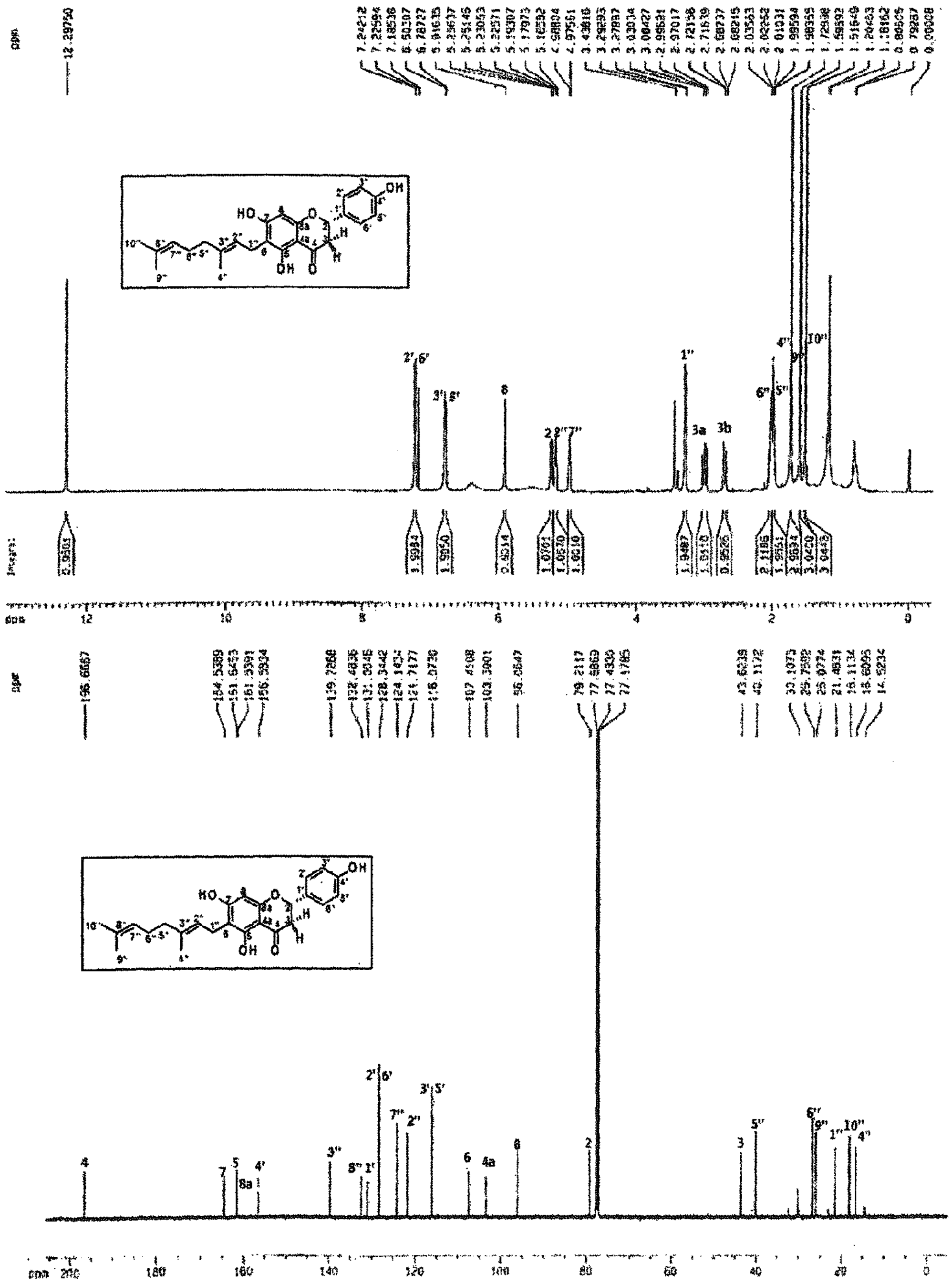
FIG. 11 shows $^{1}H$ and $^{13}C$-NMR results of an effective component (compound 7) of an extract of *Paulownia tomentosa.*
Figure 12:
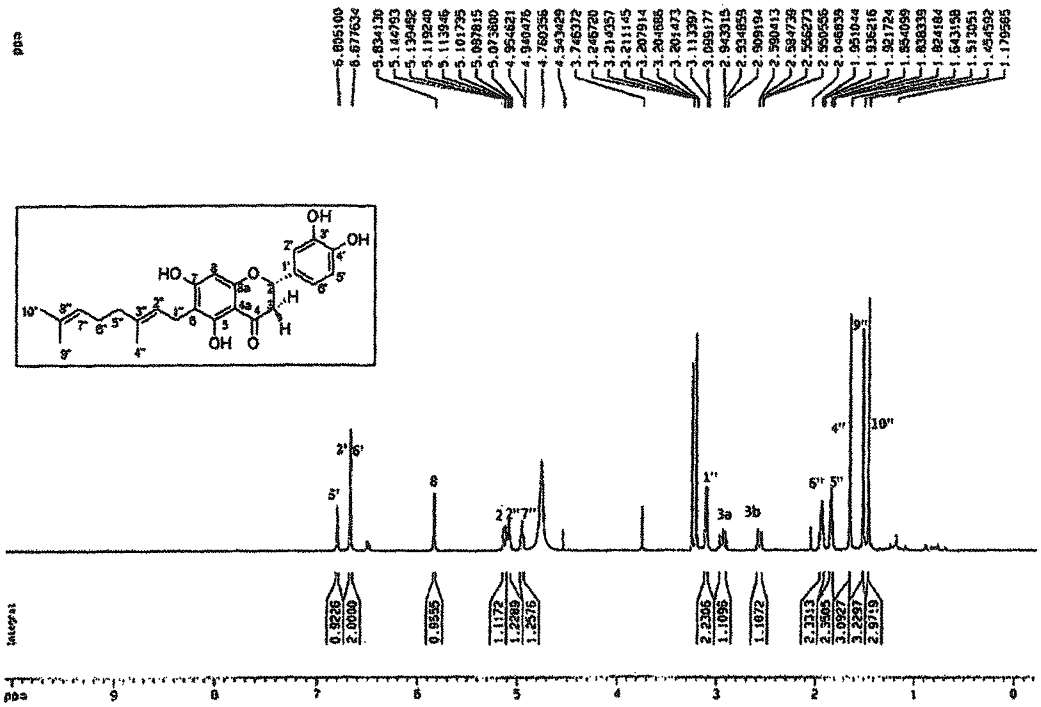
FIG. 12 shows $^{1}H$ and $^{13}C$-NMR results of an effective component (compound 8) of an extract of *Paulownia tomentosa.*
Figure 12:
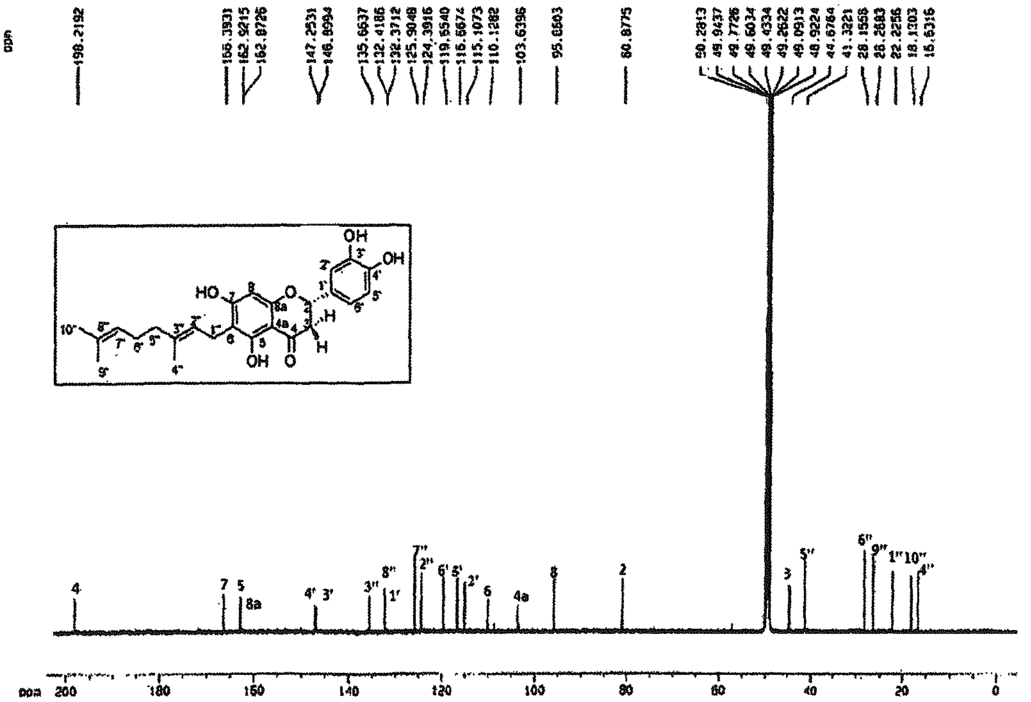
Figure 13:
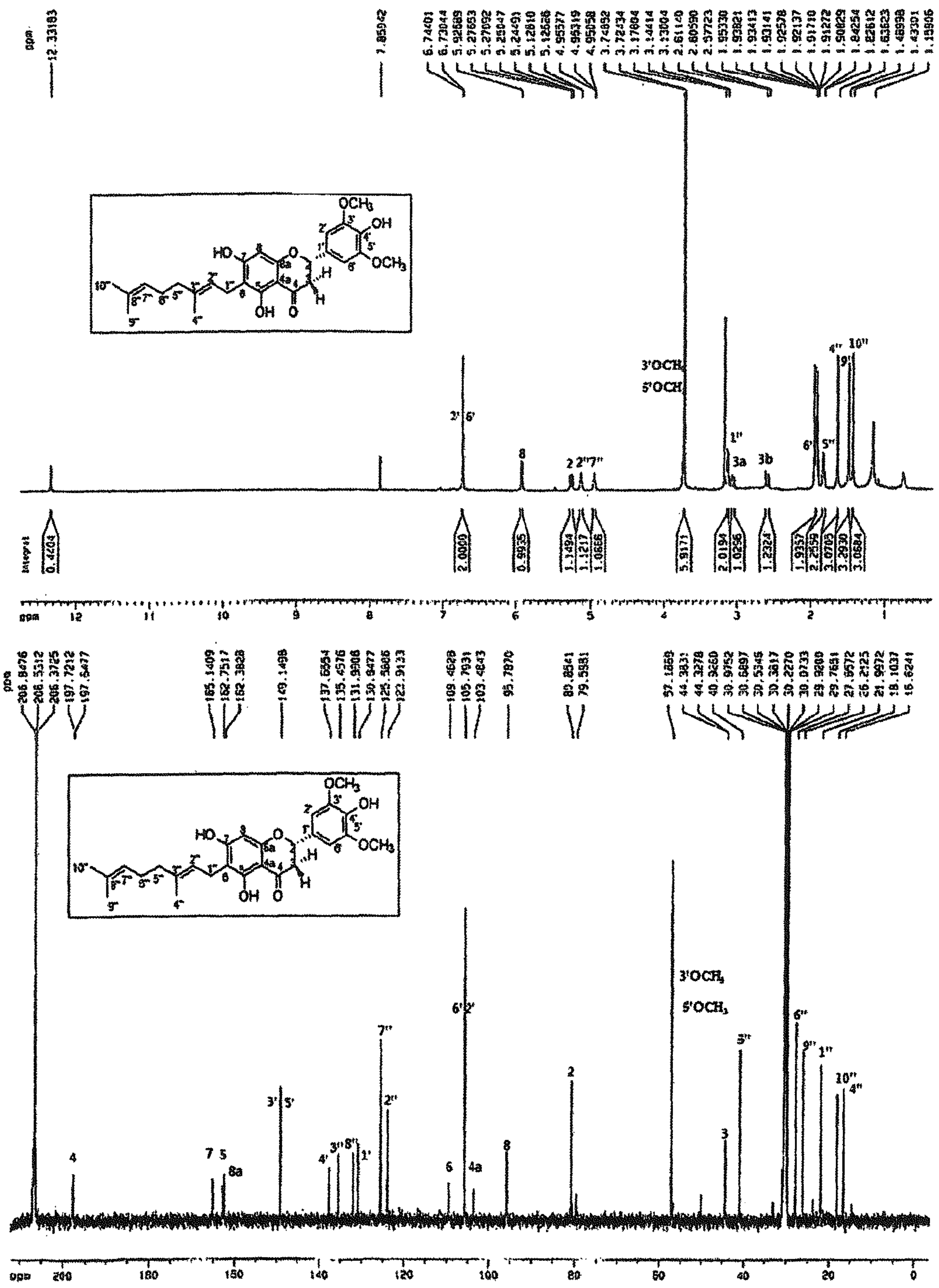
FIG. 13 shows $^{1}H$ and $^{13}C$-NMR results of an effective component (compound 9) of an extract of *Paulownia tomentosa.*

As shown in FIG. 4, it was confirmed that the straight lines of reaction rate (1/[v]) according to the concentration of inhibitors (1/[S]) meet at one point of 1/v(y axis) in Lineweaver-Burk and Dixon plots. Therefore, it was confirmed that all the compounds were typical competitive inhibitors since Vmax did not change while Km was reduced.

INDUSTRIAL APPLICABILITY

The present invention relates to a composition for inhibiting neuraminidase activity comprising geranylated flavonoids derived from *Paulownia tomentosa* as active ingredients. The extract of *Paulownia tomentosa* and geranylated flavonoids isolated from the extract exhibit significant neuraminidase inhibition activity, wherein neuraminidase plays an important role in inflammation accompanied by pathogenic viral and bacterial infections. Therefore, the extract of *Paulownia tomentosa* or geranylated flavonoids isolated from the extract can be effectively used in a composition for inhibiting neuraminidase activity as an active ingredient.

The invention claimed is:

1. A method for inhibiting neuraminidase activity, comprising administering a pharmaceutically effective amount of an extract of *Paulownia tomentosa* or a fraction thereof to an individual, wherein the neuraminidase is derived from *Clostridium perfringens*.

2. A method for inhibiting neuraminidase activity, comprising administering a pharmaceutically effective amount of a compound represented by Formula 1 or a pharmaceutically acceptable salt thereof to an individual, wherein the neuraminidase is derived from *Clostridium perfringens*,

[Formula 1]

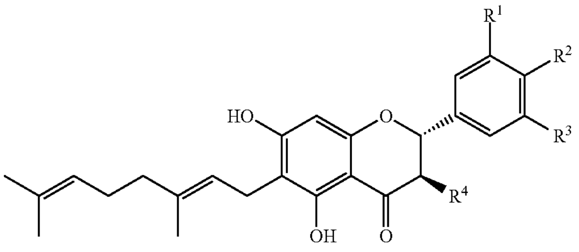

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

3. The method for inhibiting neuraminidase activity according to claim 2, wherein the compound represented by Formula I is one selected from the group consisting of Formulae 2 to 10:

[Formula 2]

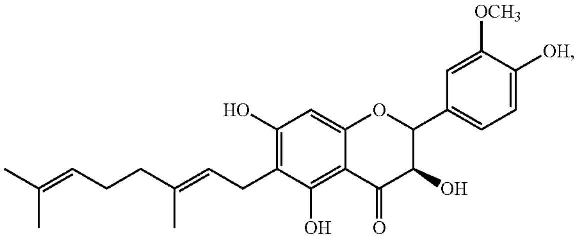

[Formula 3]

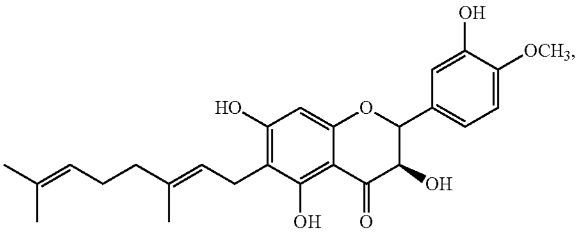

[Formula 4]

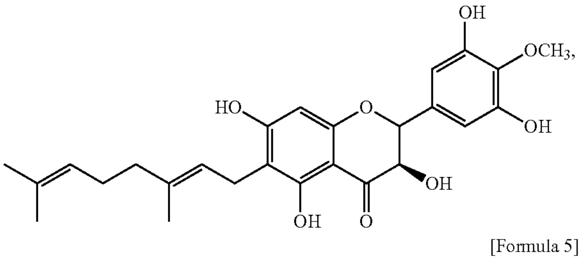

[Formula 5]

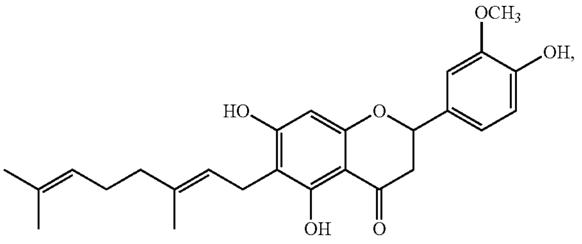

-continued

[Formula 6]

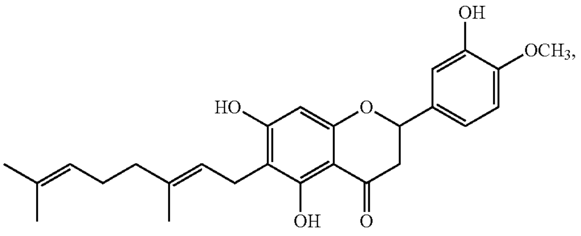

[Formula 7]

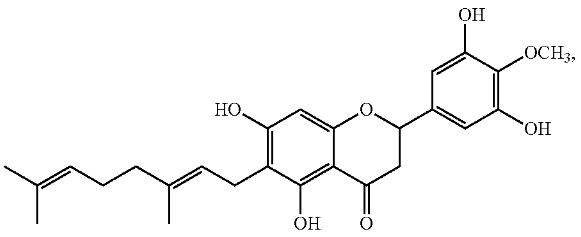

[Formula 8]

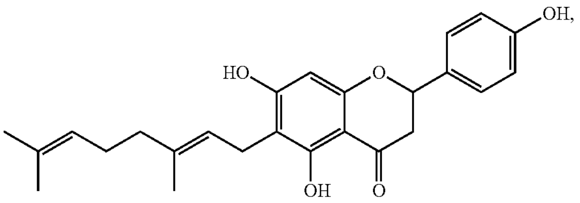

[Formula 9]

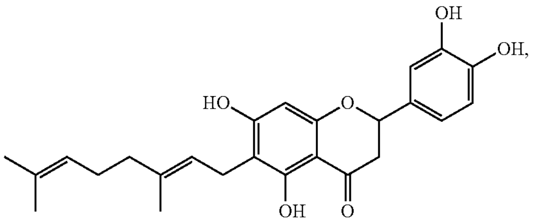

and

[Formula 10]

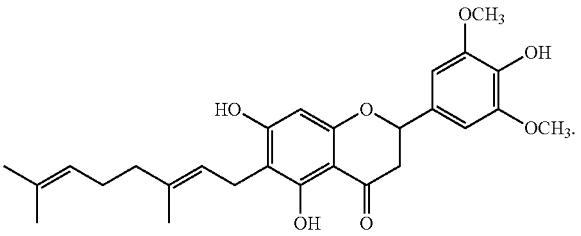

4. The method for inhibiting neuraminidase activity according to claim 2, wherein the compound represented by Formula 1 is derived from *Paulownia tomentosa*.

5. A method for treating bacterial inflammatory diseases caused by infection of *Clostridium perfringens* comprising administering a pharmaceutically effective amount of a compound represented by Formula 1 or a pharmaceutically acceptable salt thereof,

[Formula 1]

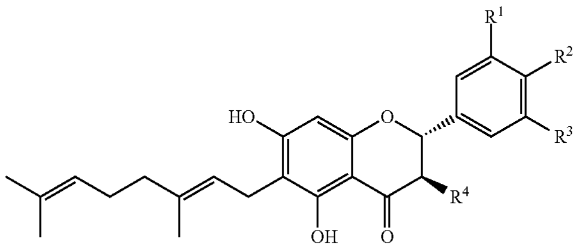

wherein $R^1$ is —H, —OH or a $C_{1-3}$ linear or branched alkoxy, $R^2$ is —OH or a $C_{1-3}$ linear or branched alkoxy, $R^3$ is —H, —OH or a $C_{1-3}$ linear or branched alkoxy, and $R^4$ is —H or —OH.

6. The method for treating bacterial inflammatory diseases caused by infection of *Clostridium perfringens* according to claim 5, wherein the compound represented by Formula 1 is one selected from the group consisting of Formulae 2 to 10:

[Formula 2]

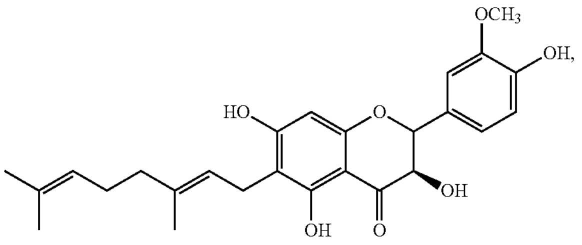

[Formula 3]

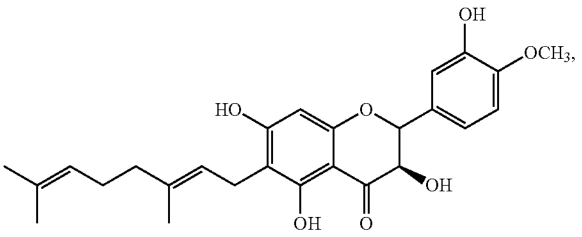

[Formula 4]

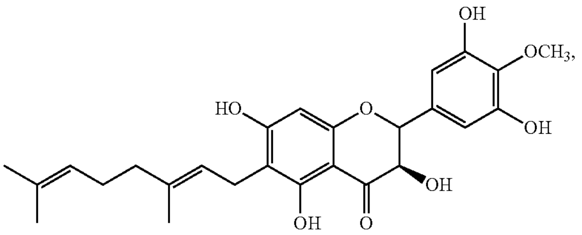

[Formula 5]

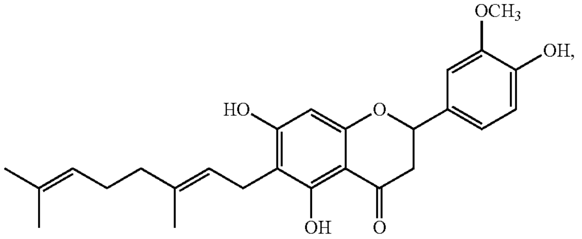

-continued

[Formula 6]

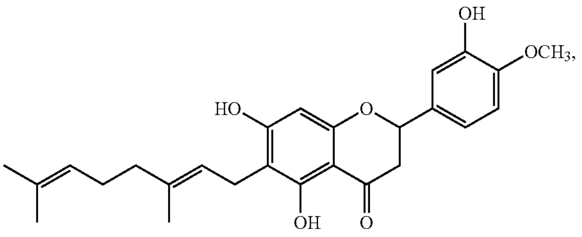

[Formula 7]

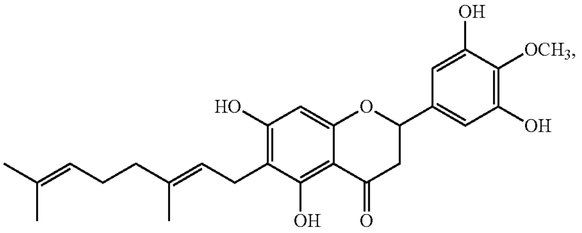

[Formula 8]

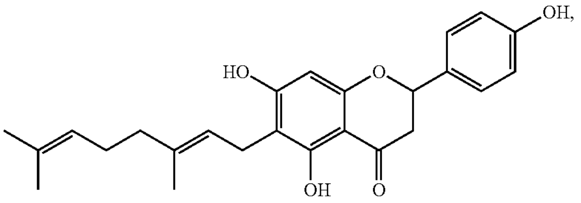

[Formula 9]

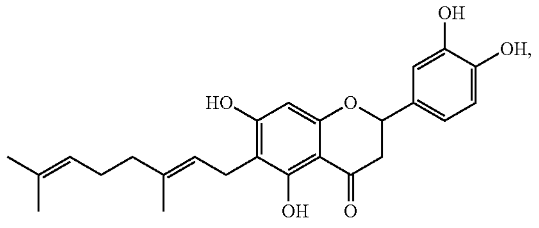

and

[Formula 10]

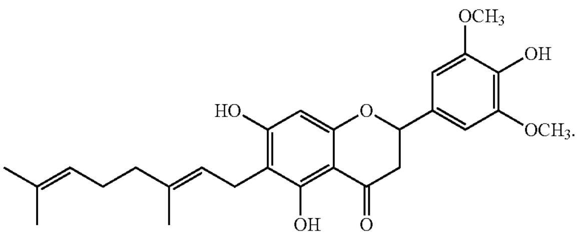

7. The method for treating bacterial inflammatory diseases caused by infection of *Clostridium perfringens* according to claim 5, wherein the compound represented by Formula 1 is derived from *Paulownia tomentosa*.

* * * * *